US007995820B2

(12) United States Patent
de Barros Carneiro et al.

(10) Patent No.: US 7,995,820 B2
(45) Date of Patent: Aug. 9, 2011

(54) SYSTEM AND METHOD FOR DETECTION OF FETAL ANATOMIES FROM ULTRASOUND IMAGES USING A CONSTRAINED PROBABILISTIC BOOSTING TREE

(75) Inventors: Gustavo Henrique Monteiro de Barros Carneiro, Plainsboro, NJ (US); Bogdan Georgescu, Plainsboro, NJ (US); Sara Good, Pleasanton, CA (US); Dorin Comaniciu, Princeton Junction, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 805 days.

(21) Appl. No.: 12/056,107

(22) Filed: Mar. 26, 2008

(65) Prior Publication Data
US 2008/0240532 A1    Oct. 2, 2008

Related U.S. Application Data

(60) Provisional application No. 60/909,057, filed on Mar. 30, 2007.

(51) Int. Cl.
*G06K 9/00* (2006.01)
(52) U.S. Cl. .................. 382/128; 382/159; 600/443
(58) Field of Classification Search .................. 382/128, 382/159, 170, 228; 600/443; 706/46, 47
See application file for complete search history.

(56) References Cited

U.S. PATENT DOCUMENTS

| 6,456,993 B1 * | 9/2002 | Freund | 706/46 |
| 7,702,596 B2 * | 4/2010 | Tu et al. | 706/20 |
| 2009/0093717 A1 * | 4/2009 | Carneiro et al. | 600/443 |
| 2011/0021915 A1 * | 1/2011 | Feng et al. | 600/443 |

OTHER PUBLICATIONS

Yefeng Zheng, et al., "Fast Automatic Heart Chamber Segmentation From 3D CT Data Using Marginal Space Learning and Steerable Features," Integrated Data Systems Department, Siemens Corporate Research, USA, Siemens Medical Solutions, Germany.
Zhuowen Tu, "Probabilistic Boosting-Tree: Learning Discriminative Models for Classification, Recognition, and Clustering," Integrated Data Systems Department, Siemens Corporation Research, Princeton, NJ 08540.
Pierre Del Moral, et al., Sequential Monte Carlo Samplers, pp. 1-29, Department of Statistics and Department of Computer Science, University of British Columbia, Vancouver, BC, Canada, Dec. 2002.

* cited by examiner

*Primary Examiner* — Louis Arana

(57) ABSTRACT

A method for detecting fetal anatomic features in ultrasound images includes providing an ultrasound image of a fetus, specifying an anatomic feature to be detected in a region S determined by parameter vector $\theta$, providing a sequence of probabilistic boosting tree classifiers, each with a pre-specified height and number of nodes. Each classifier computes a posterior probability $P(y|S)$ where $y \in \{-1,+1\}$, with $P(y=+1|S)$ representing a probability that region S contains the feature, and $P(y=-1|S)$ representing a probability that region S contains background information. The feature is detected by uniformly sampling a parameter space of parameter vector $\theta$ using a first classifier with a sampling interval vector used for training said first classifier, and having each subsequent classifier classify positive samples identified by a preceding classifier using a smaller sampling interval vector used for training said preceding classifier. Each classifier forms a union of its positive samples with those of the preceding classifier.

26 Claims, 12 Drawing Sheets a) Ellipse        b) Line a) HC b) BPD a) BPD   b) HC   c) AC   d) FL a) HL     b) CRL

FIGURE 14

TABLE I

|  | Set 1 | | | | Set 2 |
|---|---|---|---|---|---|
| Measurement | CO (mm) | IO (mm) | WI | 95% CI | CO (mm) |
| Fetal Head | | | | | |
| Hausdorff distance | 2.13 ($\sigma = 1.15$) | 2.25 ($\sigma = 0.43$) | 0.88 | (0.77, 0.98) | 2.35 ($\sigma = 2.26$) |
| Average distance | 1.44 ($\sigma = 0.77$) | 1.49 ($\sigma = 0.28$) | 0.86 | (0.75, 0.97) | 1.50 ($\sigma = 1.46$) |
| Fetal Abdomen | | | | | |
| Hausdorff distance | 2.77 ($\sigma = 1.64$) | 3.16 ($\sigma = 1.15$) | 0.89 | (0.77, 1.01) | 3.49 ($\sigma = 4.38$) |
| Average distance | 1.57 ($\sigma = 0.89$) | 1.96 ($\sigma = 0.48$) | 1.02 | (0.92, 1.12) | 2.03 ($\sigma = 2.35$) |
| Fetal Femur | | | | | |
| Hausdorff distance | 0.76 ($\sigma = 0.39$) | 0.52 ($\sigma = 0.36$) | 1.15 | (0.93, 1.37) | 1.27 ($\sigma = 2.94$) |
| Average distance | 0.51 ($\sigma = 0.26$) | 0.37 ($\sigma = 0.25$) | 1.23 | (1.04, 1.41) | 0.79 ($\sigma = 1.58$) |

FIGURE 15

TABLE II

|  | Set 3 |
|---|---|
| Measurement | CO (mm) |
| Fetal Humerus |  |
| Hausdorff distance | 2.39 ($\sigma = 1.62$) |
| Average distance | 1.69 ($\sigma = 0.09$) |
| Fetal Body |  |
| Hausdorff distance | 3.71 ($\sigma = 3.08$) |
| Average distance | 2.68 ($\sigma = 1.95$) |

TABLE III

|  | CO (mm) | CO (%) | IO (mm) | IO (%) | $r$ |
|---|---|---|---|---|---|
| BPD | 1.46 ($\sigma = 1.48$) | 1.71 ($\sigma = 1.76$) | 0.82 ($\sigma = 0.61$) | 0.97 ($\sigma = 0.59$) | 0.998 |
| HC | 4.80 ($\sigma = 4.73$) | 1.02 ($\sigma = 0.81$) | 4.11 ($\sigma = 2.57$) | 0.89 ($\sigma = 0.44$) | 0.999 |
| AC | 6.96 ($\sigma = 9.14$) | 2.43 ($\sigma = 3.51$) | 4.72 ($\sigma = 6.49$) | 1.67 ($\sigma = 2.45$) | 0.994 |
| FL | 0.45 ($\sigma = 0.71$) | 1.36 ($\sigma = 2.11$) | 0.16 ($\sigma = 0.20$) | 0.53 ($\sigma = 0.65$) | 0.996 |

FIGURE 16

TABLE IV

|     | CO (mm)           | CO (%)            | r     |
|-----|-------------------|-------------------|-------|
| BPD | 1.11 ($\sigma = 1.44$) | 1.46 ($\sigma = 1.74$) | 0.998 |
| HC  | 5.07 ($\sigma = 5.42$) | 1.25 ($\sigma = 1.34$) | 0.999 |
| AC  | 10.67 ($\sigma = 18.80$) | 3.00 ($\sigma = 6.16$) | 0.991 |
| FL  | 0.89 ($\sigma = 2.78$) | 2.11 ($\sigma = 5.68$) | 0.986 |
| HL  | 1.59 ($\sigma = 1.53$) | 3.52 ($\sigma = 3.72$) | 0.982 |
| CRL | 2.10 ($\sigma = 1.85$) | 3.84 ($\sigma = 3.06$) | 0.965 |

TABLE V

|     | WI     | 95% CI             | P    | 95% CI         |
|-----|--------|--------------------|------|----------------|
| BPD | 0.8246 | (0.5791, 1.0702)   | 80.0 | (75.38, 84.68) |
| HC  | 1.0567 | (0.8924, 1.2211)   | 80.0 | (75.38, 84.68) |
| AC  | 0.7086 | (0.4520, 0.9652)   | 50.0 | (44.14, 55.86) |
| FL  | 0.9201 | (0.5774, 1.2628)   | 60.0 | (54.26, 65.74) |

SYSTEM AND METHOD FOR DETECTION OF FETAL ANATOMIES FROM ULTRASOUND IMAGES USING A CONSTRAINED PROBABILISTIC BOOSTING TREE

CROSS REFERENCE TO RELATED UNITED STATES APPLICATIONS

This application claims priority from "Automatic Fetal Measurements in Ultrasound Using Constrained Probabilistic Boosting Tree", U.S. Provisional Application No. 60/909,057 of Carneiro, et al., filed Mar. 30, 2007, the contents of which are herein incorporated by reference in their entirety.

TECHNICAL FIELD

This disclosure is directed to the automatic detection and measurement of fetal anatomical structures in ultrasound images.

DISCUSSION OF THE RELATED ART

Accurate fetal ultrasound measurements are one of the most important factors for high quality obstetrics health care. These measurements offer a myriad of challenges, including: difficulty of modeling the appearance variations of the visual object of interest; robustness to speckle noise and signal drop-out; and the large search space of the detection procedure. Previous solutions typically rely on the explicit encoding of prior knowledge and formulation of the task as a perceptual grouping task solved through clustering or variational approaches. These methods are constrained by the validity of the underlying assumptions and usually are insufficient to capture the complex appearances of fetal anatomies.

Common fetal ultrasound measurements include: bi-parietal diameter (BDP), head circumference (HC), abdominal circumference (AC), femur length (FL), humerus length (HL), and crown rump length (CRL). These measures are used to estimate both the gestational age (GA) of the fetus, i.e., the length of pregnancy in weeks and days, and also as an important diagnostic auxiliary tool. Accurate estimation of GA is important to estimate the date of confinement, to estimate the expected delivery date, to assess the fetal size, and to monitor the fetal growth. The current workflow requires expert users (e.g., sonographers) to perform those measurements manually, resulting in the following issues: (1) the quality of the measurements are user-dependent; (2) the exam can take more than 30 minutes; and (3) the expert users can suffer from Repetitive Stress Injury (RSI) due to these lengthy exams. Therefore, the automation of the ultrasound measures mentioned above has the potential of: (1) improving everyday workflow to increase patient throughput and productivity; (2) improving accuracy and consistency of measurements, bringing expert-like consistency to every exam, which leads to more robust decision support; and (3) reduce the risk of RSI to specialists.

SUMMARY OF THE INVENTION

Exemplary embodiments of the invention as described herein generally include methods and systems for the automatic detection and measurement of fetal anatomical structures in ultrasound images. A system for fast automatic detection and measurement of fetal anatomies according to an embodiment of the invention directly exploits a large database of expert annotated fetal anatomical structures in ultrasound images. Such a method learns to automatically distinguish between the appearance of the object of interest and background by training a constrained probabilistic boosting tree classifier, and is able to produce the automatic segmentation of several fetal anatomies using the same basic detection algorithm.

A method according to an embodiment of the invention targets the automatic on-line detection and segmentation of fetal head, abdomen, femur, humerus, and fetal body in typical ultrasound images, which are then used to compute BDP and HC for head, AC for abdomen, FL for femur, HL for humerus, and CRL for the fetal body. The automatic measurements provided by the system should be on average as precise as those done by an expert user, such as a clinician or a sonographer. A method according to an embodiment of the invention should be: (1) efficient, in that the system should run under one second; (2) robust to the appearance variations of the visual object of interest; (3) robust to speckle noise and signal drop-out typical in ultrasound images; and (4) segmentation accuracy. Moreover, a basic algorithm according to an embodiment of the invention should be the same for the segmentation of the different anatomies aforementioned in order to facilitate the extension of this system to other fetal anatomies.

An approach according to an embodiment of the invention directly exploits the expert annotation of fetal anatomical structures in large databases of ultrasound images in order to train a sequence of discriminative classifiers. The classifier used is based on a constrained version of the probabilistic boosting tree. An approach according to an embodiment of the invention is designed to be completely automatic. This means that the user need not provide any type of initial guess. The only inputs to the system are the image and the measurement to be performed (BPD, HC, AC, FL, HL, or CRL).

Results are shown on fully automatic measurement of biparietal diameter (BPD), head circumference (HC), abdominal circumference (AC), femur length (FL), humerus length (HL), and crown rump length (CRL). An approach according to an embodiment of the invention is the first to deal with the HL and CRL measurements. Extensive experiments (with clinical validation) show that a system according to an embodiment of the invention is, on average, close to the accuracy of experts in terms of segmentation and obstetric measurements. Finally this system runs under half second on a standard dual-core PC computer.

According to an aspect of the invention, there is provided a method for detecting fetal anatomic features in ultrasound images, including providing a plurality of ultrasound images of a fetus, each said image comprising a plurality of intensities associated with a 2-dimensional grid, providing a parameter vector specifying a region of interest S containing an anatomic feature of interest for each of said plurality of images, training a sequence of probabilistic boosting tree classifiers, each with a pre-specified height and number of nodes, wherein each classifier is trained with a set of positive feature samples and a set of negative feature samples generated for each of said plurality of images by randomly sampling a parameter subspace, wherein each classifier computes a posterior probability $P(y|S)$ where $y \in \{-1,+1\}$, with $P(y=+1|S)$ representing a probability that the image region S contains the feature of interest, and $P(y=-1|S)$ representing a probability that image region S contains background information, and detecting said anatomic feature of interest in a new ultrasound image using said probabilistic boosting tree classifiers.

According to a further aspect of the invention, each region of interest (ROI) S is determined by parameter vector $\theta = [x, y,$ α, $\sigma_x$, $\sigma_y$], wherein (x, y) represent a top left position in said ROI, α denotes an orientation of said ROI, and ($\sigma_x$, $\sigma_y$) represent a scale of said ROI.

According to a further aspect of the invention, the sequence of probabilistic boosting tree classifiers comprises an ROI classifier, a coarse classifier, and a fine classifier.

According to a further aspect of the invention, the ROI classifier is trained on positive samples located in a parameter subspace defined by $\Delta_+^{ROI} = [\Delta_x^{ROI}, \Delta_y^{ROI}, X, \Delta_{\sigma_x}^{ROI}, X]$, wherein $$\Delta_x^{ROI} \epsilon [x-\delta_x^{ROI}, x+\delta_x^{ROI}],$$

$$\Delta_y^{ROI} \epsilon [y-\delta_y^{ROI}, y+\delta_y^{ROI}],$$

$$\Delta_{\sigma_x}^{ROI} \epsilon [\sigma_x-\delta_{\sigma_x}^{ROI}, \sigma_x+\delta_{\sigma_x}^{ROI}],$$

and X represents parameters α, $\sigma_y$ not learned by said ROI classifier, and said ROI classifier is trained on negative samples located in a parameter subspace defined by $\Delta_-^{ROI} = \Theta - \Delta_+^{ROI}$, wherein $\Theta$ represents an entire parameter space spanned by parameter vector θ, wherein the ROI classifier detects the position and scale of the feature of interest.

According to a further aspect of the invention, the coarse classifier is trained with positive samples from a parameter subset defined by $\Delta_+^{coarse} = [\Delta_x^{coarse}, \Delta_y^{coarse}, \Delta_\alpha^{coarse}, \Delta_{\sigma_x}^{coarse}, \Delta_{\sigma_y}^{coarse}]$, where $$\Delta_x^{coarse} \epsilon [x-\delta_x^{coarse}, x+\delta_x^{coarse}],$$

$$\Delta_y^{coarse} \epsilon [y-\delta_y^{coarse}, y+\delta_y^{coarse}],$$

$$\Delta_\alpha^{coarse} \epsilon [\alpha-\delta_\alpha^{coarse}, \alpha+\delta_\alpha^{coarse}],$$

$$\Delta_{\sigma_x}^{coarse} \epsilon [\sigma_x-\delta_{\sigma_x}^{coarse}, \sigma_x+\delta_{\sigma_x}^{coarse}],$$

$$\Delta_{\sigma_y}^{coarse} \epsilon [\sigma_y-\delta_{\sigma_y}^{coarse}, \sigma_y+\delta_{\sigma_y}^{coarse}],$$

wherein $\delta^{coarse} < \delta^{ROI}$ for all parameters, and wherein said coarse classifier is trained with negative samples in a parameter subspace defined by $\Delta_-^{coarse} = \Delta_-^{ROI} - \Delta_+^{coarse}$.

According to a further aspect of the invention, the fine classifier is trained with positive samples from a parameter subset defined by $\Delta_+^{fine} [\Delta_x^{fine}, \Delta_y^{fine}, \Delta_\alpha^{fine}, \Delta_{\sigma_x}^{fine}, \Delta_{\sigma_y}^{fine}]$, wherein $$\Delta_x^{fine} \epsilon [x-\delta_x^{fine}, x+\delta_x^{fine}],$$

$$\Delta_y^{fine} \epsilon [y-\delta_y^{fine}, y+\delta_y^{fine}],$$

$$\Delta_\alpha^{fine} \epsilon [\alpha-\delta_\alpha^{fine}, \alpha+\delta_\alpha^{fine}],$$

$$\Delta_{\sigma_x}^{fine} \epsilon [\sigma_x-\delta_{\sigma_x}^{fine}, \sigma_x+\delta_{\sigma_x}^{fine}],$$

$$\Delta_{\sigma_y}^{fine} \epsilon [\sigma_y-\delta_{\sigma_y}^{fine}, \sigma_y+\delta_{\sigma_y}^{fine}],$$

wherein $\delta^{fine} < \delta^{coarse}$ for all parameters, and wherein said fine classifier is trained with negative samples in a parameter subspace defined by $\Delta_-^{fine} = \Delta_-^{coarse} - \Delta_+^{fine}$.

According to a further aspect of the invention, detecting said anatomic feature of interest comprises uniformly sampling a parameter space of parameter vector θ using said ROI classifier with a sampling interval vector used for training said ROI classifier, having said coarse classifier classify positive samples identified by said ROI classifier using a smaller sampling interval vector used for training said coarse classifier, and having said fine classifier classify positive samples identified by said coarse classifier using a smaller sampling interval vector used for training said fine classifier, wherein each classifier forms a union of its positive samples with those positive samples of the previous classifier.

According to a further aspect of the invention, the method includes selecting a positive sample from said fine classifier with a highest probability as representing said anatomic feature of interest if said positive sample probability is greater than a predetermined threshold.

According to a further aspect of the invention, the anatomic feature of interest is one or more of a bi-parietal diameter, a head circumference, an abdominal circumference, a femur length, a humerus length, and a crown rump length.

According to another aspect of the invention there is provided a method for detecting fetal anatomic features in ultrasound images, including providing an ultrasound image of a fetus, said image comprising a plurality of intensities associated with a 2-dimensional grid, specifying an anatomic feature of interest to be detected in a region of interest S in said image determined by parameter vector θ, providing a sequence of probabilistic boosting tree classifiers, each with a pre-specified height and number of nodes, wherein each classifier computes a posterior probability P(y|S) where y∈{−1,+1}, with P(y=+1|S) representing a probability that region of interest S contains the feature of interest, and P(y=−1|S) representing a probability that region of interest S contains background information, and detecting said anatomic feature of interest by uniformly sampling a parameter space of parameter vector θ using a first classifier with a sampling interval vector used for training said first classifier, and having each subsequent classifier of said sequence of classifiers classify positive samples identified by a preceding classifier using a smaller sampling interval vector used for training said preceding classifier, wherein each classifier forms a union of its positive samples with those positive samples of the preceding classifier.

According to a further aspect of the invention, the method includes training said sequence of probabilistic boosting tree classifiers on a plurality of training ultrasound images using a set of positive feature samples and a set of negative feature samples generated for each of said plurality of images by randomly sampling a parameter subspace, wherein a sampling interval for each classifier is finer than a sampling interval for a preceding classifier, and a sampling region for each classifier contains the sampling region for each subsequent classifier.

According to a further aspect of the invention, the region of interest (ROI) is determined by parameter vector θ=[x, y, α, $\sigma_x$, $\sigma_y$], wherein (x, y) represent a top left position in said ROI, α denotes an orientation of said ROI, and ($\sigma_x$,$\sigma_y$) represent a scale of said ROI.

According to a further aspect of the invention, the method includes selecting a positive sample from said fine classifier with a highest probability as representing said anatomic feature of interest if said positive sample probability is greater than a predetermined threshold.

According to another aspect of the invention, there is provided a program storage device readable by a computer, tangibly embodying a program of instructions executable by the computer to perform the method steps for detecting fetal anatomic features in ultrasound images.

BRIEF DESCRIPTION OF THE DRAWINGS

FIG. 14 presents Table I of result data, according to an embodiment of the invention.

FIG. 15 presents Tables II and III of result data, according to an embodiment of the invention.

FIG. 16 presents Tables IV and V of result data, according to an embodiment of the invention.

DETAILED DESCRIPTION OF EXEMPLARY EMBODIMENTS

Figure 1:
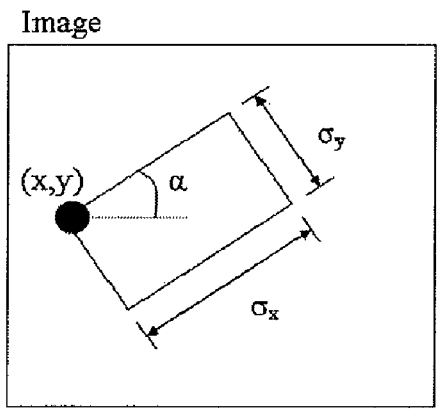
FIG. 1 illustrates the parameters that define a rectangular foreground region of an image, according to an embodiment of the invention.

Exemplary embodiments of the invention as described herein generally include systems and methods for quasi-real time measurements of ventricular dimensions from M-mode echocardiograms. Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

As used herein, the term "image" refers to multi-dimensional data composed of discrete image elements (e.g., pixels for 2-D images and voxels for 3-D images). The image may be, for example, a medical image of a subject collected by computer tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^3$ to R, the methods of the inventions are not limited to such images, and can be applied to images of any dimension, e.g., a 2-D picture or a 3-D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

A method according to an embodiment of the invention exploits the database-guided segmentation paradigm in the domain of fetal ultrasound images. This domain presents common issues encountered in cardiac ultrasound images, such as large amount of noise, signal drop-out and large variations between the appearance, configuration and shape of the anatomical structure. However, a method according to an embodiment of the invention can handle new challenges presented by fetal ultrasound images, such as the extreme appearance variability of the fetal abdomen and fetal body imaging, generalization of the same basic detection algorithm to all anatomical structures, and extreme efficiency. To meet these new challenges, the recently proposed probabilistic boosting tree classifier was constrained to limit the number of nodes present in the binary tree, and also to divide the original classification into hierarchical stages of increasing complexity.

Automatic Measurement of Fetal Anatomy

A method according to an embodiment of the invention is based on a learning process that implicitly encodes the knowledge embedded in expert annotated databases. This learning process produces models that are used in the segmentation procedure. The segmentation is then posed as a task of structure detection, where an image region containing the sought structure is automatically segmented. The fetal measurements can then be derived from this region.

A method according to an embodiment of the invention can provide a segmentation of the most likely rectangular image region containing the anatomical structure of interest. From this rectangular region, it is possible to determine the measurements of interest (i.e., BPD, HC, AC, FL, HL, and CRL), as shown below. The following definition of segmentation is used: assume that the image domain is defined by $I:R^{N\times M}\to R$ with N denoting the number of rows and M the number of columns, then the segmentation task determines the sets S, $B \subset I$, where S represents the foreground region (i.e., the structure of interest), and B represents the background. The sets satisfy the constraint $S \cup B = I$, where $S \cap B = \emptyset$. The foreground image region S is determined by the following vector:

$$\theta = [x, y, \alpha, \sigma_x, \sigma_y], \quad (1)$$

where the parameters (x, y) represent the top left region position in the image, $\alpha$ denotes orientation, and $(\sigma_x, \sigma_y)$, the region scale. These parameters are illustrated in FIG. 1, which shows an image with a rectangular foreground region.

Figure 2:
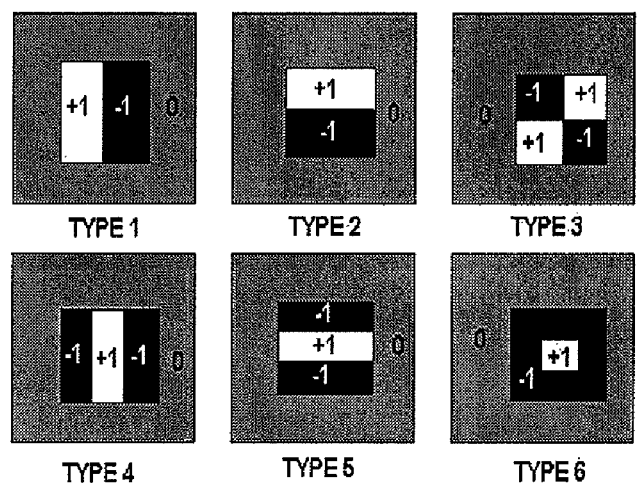
FIG. 2 illustrates some exemplary, non-limiting feature types used in an embodiment of the invention

The appearance of the image region can be represented with features derived from Haar wavelet, which have the following properties: (1) good modeling power for the different types of visual patterns, such as pedestrians, faces, and left ventricles in ultrasound images; and (2) computation efficiency with the use of integral images. FIG. 2 illustrates some exemplary, non-limiting feature types used in an embodiment of the invention, where each feature is denoted by the following feature vector:

$$\theta_f = [t, x_f, x_f, d_x, d_y, s], \quad (2)$$

where $t \in \{1, \ldots, 6\}$ denotes the feature type, $(x_f, y_f)$ is the top-left coordinate of the feature location within S defined by $\theta$ in EQ. (1) (i.e., $x_f \in [1, 1+(\sigma_x - d_x)]$ and $y_f \in [1, 1+(\sigma_y - d_y)]$), $d_x$, $d_y$ are the length and width of the spatial support of the feature with $d_x \in [1, \sigma_x]$ and $d_y \in [1, \sigma_y]$ (note that $\sigma_{\{x,y\}}$ is defined in EQ. (1)), and $s \in \{+1, -1\}$ represents the two versions of each feature with its original or inverted signs. Note that the feature has the same orientation $\alpha$ as the image region.

The output value of each feature is the difference between the image pixels lying in the white section, represented by +1 in FIG. 2, and the image pixels in the black section, represented by −1 in FIG. 2. The gray regions in FIG. 2 represent the foreground region S. The feature value can be efficiently computed using integral images. An integral image can be computed as follows:

$$T(x, y) = \sum_{i=0}^{x} \sum_{j=0}^{y} I(x, y), \quad (3)$$

where $T: R^{N \times M} \rightarrow R$ denotes the integral image. Then the feature value is computed efficiently through a small number of additions and subtractions. For example, the feature value of feature type 1 in FIG. 2 can be computed as $$f(\theta_f) = T_f^+ - T_f^-$$

where $$T_f^+ = T\left(x_f + \frac{d_x}{2}, y_f + d_y\right) + T(x_f, y_f) - T\left(x_f + \frac{d_x}{2}, y_f\right) - T(x_f, y_f + d_y),$$

$$T_f^- = T(x_f + d_x, y_f + d_y) + T\left(x_f + \frac{d_x}{2}, y_f\right) - T(x_f + d_x, y_f) - T\left(x_f + \frac{d_x}{2}, y_f + d_y\right).$$

This means that the integral image is computed once and each feature value involves the addition and subtraction of six values from the integral image. The original image is rotated in intervals of $\delta_\alpha$ (according to an exemplary, non-limiting embodiment of the invention, $\delta_\alpha = 10°$) and an integral image is computed for each rotated image. These rotations and integral image computations can be pre-processed. Taking into account all possible feature types, locations, and sizes, there can be in the order of $10^5$ possible features within a region.

A classifier then defines the following function: $P(y|S)$, where $y \in \{-1, +1\}$ with $P(y=+1|S)$ representing the probability that the image region S contains the structure of interest (i.e., a positive sample), and $P(y=-1|S)$, the probability that the image region S contains background information (i.e., a negative sample). A method according to an embodiment of the invention determines $$\theta^* = \arg\max_\theta P(y|S), \quad (4)$$

where S is the foreground image region defined by $\theta$ in EQ. (1). Therefore, a method according to an embodiment of the invention can train a discriminative classifier that minimizes the following probability of mis-classification:

$$P(\text{error}) = \int_\theta P\left(\text{error}|\theta\right) P(\theta) d\theta, \text{ where}$$

-continued $$P(\text{error}|\theta) = \begin{cases} +1 & \text{if } y \neq \tilde{y}, \\ 0 & \text{otherwise}, \end{cases}$$

with $$y = \arg\max_{y \in \{-1,+1\}} P(y|S)$$

and $\tilde{y}$ being the correct response for the parameter value $\theta$.

Probabilistic Boosting Tree

According to an embodiment of the invention, the classifier used for the anatomical structure detection is derived from the probabilistic boosting tree classifier (PBT). This classifier is described Z. Tu., "Probabilistic boosting-tree: learning discriminative models for classification, recognition, and clustering", *International Conference on Computer Vision*, Vol. 2, pp. 1589-1596, 2005, the contents of which are herein incorporated by reference in their entirety. The PBT classifier is a boosting classifier, where the strong classifiers are represented by the nodes of a binary tree. The PBT can cluster data automatically, allowing for a binary classification of data sets presenting multi-modal distributions. Another property of the PBT classifier is that after training, the posterior probability can be used as a threshold to balance between precision and recall.

Training the PBT involves a recursive construction of a binary tree, where each of the nodes represents a strong classifier. Each node can be trained with an AdaBoost algorithm, which automatically trains a strong classifier by combining a set of weak classifiers $$H(S) = \sum_{t=1}^{T} \omega_t h_t(S),$$

where S is an image region determined by $\theta$ in EQ. (1), $h_t(S)$ is the response of a weak classifier, and $\omega_t$ is the weight associated with each weak classifier. By minimizing the probability of error, the AdaBoost classifier automatically selects the weak classifiers and their respective weights. The probabilities computed by each strong classifier is then denoted as follows:

$$q(+1|S) = \frac{\exp(2H(S))}{1 + \exp(2H(S))} \text{ and } q(-1|S) = \frac{\exp(-2H(S))}{1 + \exp(-2H(S))} \quad (5)$$

Figure 3:
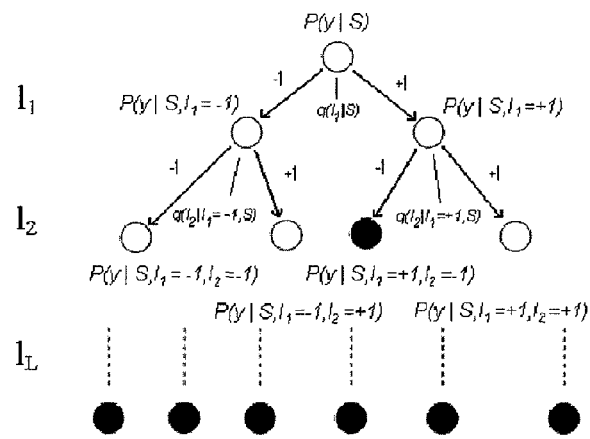
FIG. 3 shows an exemplary, non-limiting PBT binary tree, according to an embodiment of the invention.

The posterior probability that a region S is foreground (y=+1), or background (y=−1) is computed as:

$$P(y|S) = \sum_{l_1, l_2, \ldots, l_n} P(y|l_n, \ldots, l_1, S) \ldots q(l_2|l_1, S) q(l_1|S) \quad (6)$$

where n is the total number of nodes of the tree, and $l \in \{-1, +1\}$. An exemplary, non-limiting PBT binary tree is shown in FIG. 3. The dark nodes are the leaf nodes. Each level of the tree corresponds to an augmented variable. Each tree node is a strong classifier. The goal of the learning algorithm is to learn the posterior distribution $p(y|S)$. Each tree level $l_i$ is an augmented variable:

$$\tilde{p}(y|S)) = \sum_{l_1} \tilde{p}(y|l_1, S) q(l_1|S)$$

$$= \sum_{l_1, l_2} \tilde{p}(y|l_2, l_1, S) q(l_2|l_1, S) q(l_1|S)$$

$$= \sum_{l_1, \ldots, l_n} \tilde{p}(y|l_n, \ldots, l_1, S) \ldots q(l_2|l_1, x) q(l_1|S).$$

At a tree node, if the exact model can be learned, then $$P(y|l_n, \ldots, l_1, S) = \sum_{l_{i+1}} \delta(y = l_{i+1}) q(l_{i+1}|l_i, \ldots, l_1, S) \text{ where}$$

$$\delta(x) = \begin{cases} 1, & \text{if } x = \text{true}, \\ 0, & \text{otherwise}. \end{cases}$$

This means the model $q(l_{i+1}|l_i, \ldots l_1, x)$ perfectly predicts the y and the tree can stop expanding. The augmented variables $l_i$ gradually decouples y from x to make a better prediction. Note that the value $q(l_{i+1}|l_i, \ldots, l_1, S)$ is obtained by computing the value of $q(l_{i+1}|S)$ at a PBT node reached following the path $l_1 \rightarrow l_2 \rightarrow, \ldots, l_i$, with $l_1$ representing the root node and $l \in \{-1, +1\}$, as shown in FIG. 3.

The original PBT classifier has the following feature: if it is challenging to find a function that robustly separates positive from negative samples, the tree can become overly complex, which can cause: (1) overfit of the training data in the nodes close to the leaves; (2) a long training procedure; and (3) a long detection procedure. The overfit of the data in the leaf nodes happens because of the limited number of training samples remaining to train those classifiers. The number of strong classifiers to train grows exponentially with the number of tree levels, which in turn grows with the complexity of the classification task, hence the training process can take long time for complex classification tasks. Finally, note that for each sample θ from EQ. (1) to be evaluated during detection, it is necessary to compute the probability over all the nodes of the classification tree. As a result, it is necessary to compute P(y|S) for $N_\theta = N_x \times N_y \times N_\alpha \times N_{o_x} \times N_{o_y}$ times, where $N_\theta$ denotes the number of sampling points to evaluate. Usually, $N_\theta$ is in the order of $10^8$, which can have an impact in the running time of the algorithm. For example, in a standard dual-core computer the probability computation of $10^8$ samples using a full binary PBT classifier of height five can take around 10 seconds, above a target of less than one second.

Constrained Probabilistic Boosting Tree

According to an embodiment of the invention, there is a two-part solution to the challenges mentioned above. A first part is based on dividing the parameter space into subspaces, simplifying both the training and testing procedures. A second part comprises constraining the growth of the tree by limiting the height and number of nodes. This solution decreases learning and detection times and improves the generalization of the classifier, as shown below.

Figure 4:
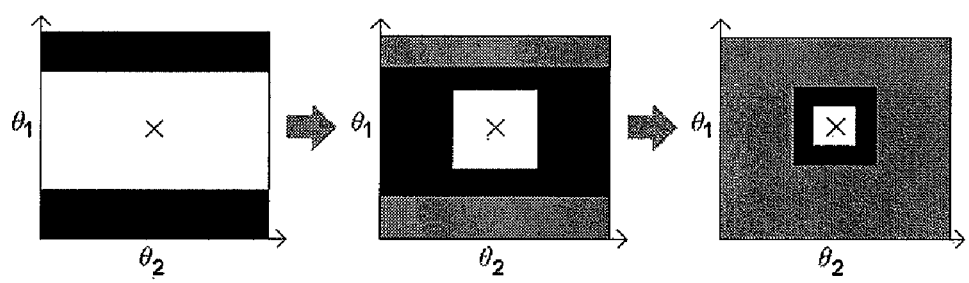
FIG. 4 illustrates a simple to complex strategy using a 2-dimensional parameter space, according to an embodiment of the invention.

Observing that "visual processing in the cortex is classically modeled as a hierarchy of increasingly sophisticated representations", a simple-to-complex classification scheme is designed. Assuming that the parameter space is represented by Θ, the idea is subdivide this initial space into subspaces $\Theta_1 \subset \Theta_2 \subset \ldots \subset \Theta_T \subset \Theta$, where the classification problem grows in terms of complexity from $\Theta_1$ to $\Theta_T$. By implementing this strategy, the training and detection algorithms can be several orders of magnitude more efficient without damaging the accuracy of the approach. FIG. 4 illustrates a simple to complex strategy using a 2-dimensional parameter space, where the target parameter values are represented by the position X. From left to right, the first graph shows two regions in the parameter space: the black area containing the negative samples, and the white area with the positive samples. Notice that in this first graph, the training and detection happen only for the parameter $\theta_1$. The second graph shows a training and detection using both parameters, where the positive samples are acquired from the center of the white circle around position X, and negatives are the samples in the black region. The gray area is a no sampling zone. The last graph shows another classification in the parameter space, with positive and negatives samples closer to the position X. As described herein below, these three graphs can be related to the region of interest (ROI) classifier, coarse classifier, and fine classifier, respectively. Notice that the idea is to train different classifiers, where the first stages tend to be robust and less accurate, and the last stages are more accurate and more complex. The first stages are trained with a subset of the initial set of parameters instead of a subspace of the full parameter space. Classifiers are trained using a subspace of the full parameter space only in the last stages.

Each subset and subspace is designed to have in the order of $10^4$ to $10^5$ parameter space samples to be evaluated, which results in a reduction of three orders of magnitude compared to the initial number of samples mentioned above. Moreover, the initial classifiers are presented with relatively simple classification tasks that produces classification trees of low complexity, and consequently the probability computation in these trees are faster than in subsequent trees. Finally, given that the classification task of each classifier is less complex than the original task, the height and the number of tree nodes can be constrained. These implementations reduce the training and detection times, and improve the generalization ability of the classifier. This resulting classifier is referred to herein below as a Constrained PBT (CPBT).

Annotation Protocol

Figure 6:
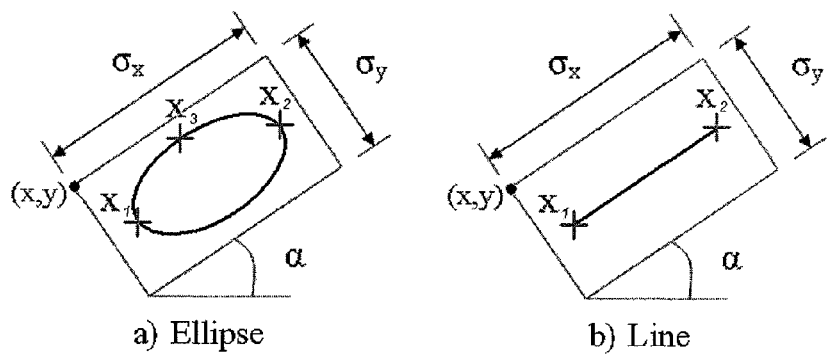
FIGS. 6(a)-(b) illustrates exemplary ellipse and line annotations, according to an embodiment of the invention.

Sonographers and clinicians have representations for the BPD, HC, AC, FL, HL, and CRL measures. That is, HC and AC are represented with an ellipse, and BPD, FL, HL, and CRL, with a line. FIGS. 5(a)-(f) shows expert annotations for the BPD, HC, AC, FL, HL, and CRL measurements, respectively. These annotations follow the American Institute of Ultrasound in Medicine (AIUM) guidelines. These annotations explicitly define the parameter θ in EQ. (1) for the positive sample of the training image as follows. FIGS. 6(a)-(b) illustrates exemplary ellipse and line annotations.

For the ellipsoidal measurements, the user defines three points: $x_1$ and $x_2$, as shown in FIG. 6(a), defining the major axis, and $x_3$, defining one point of the minor axis. With $x_1$ and $x_2$, one can compute the center of the ellipse $$x_c = \frac{x_1 + x_2}{2},$$

then the region parameters of EQ. (1) are computed as follows:

$$\sigma_x = 2\kappa \times \|x_1 - x_c\| \quad (7)$$

$$\sigma_y = 2\kappa \times \|x_3 - x_c\|$$

-continued $$\alpha = \cos^{-1}\left(\frac{(x_1 - x_c) \cdot (1,0)}{\|x_1 - x_c\|}\right)$$

$$x = x_c - \frac{\sigma_x}{2}\cos(\alpha)$$

$$y = y_c - \frac{\sigma_y}{2}\sin(\alpha)$$

where x represents a two-dimensional vector, • represent vector dot product, $\kappa>1$ such that a region comprises the anatomy plus some margin, (1, 0) denotes the horizontal unit vector, and $x_c=(x_c, y_c)$.

For the line measurements, the user defines two points: $x_1$ and $x_2$, as shown in FIG. 6(b). With $x_1$ and $x_2$, one can compute the center $$x_c = \frac{x_1 + x_2}{2},$$

and the region parameters of EQ. (1) are computed as follows:

$$\sigma_x = 2\kappa \times \|x_1 - x_c\| \quad (8)$$

$$\sigma_y = 2\kappa\sigma_x$$

$$\alpha = \cos^{-1}\left(\frac{(x_1 - x_c) \cdot (1,0)}{\|x_1 - x_c\|}\right)$$

$$x = x_c - \frac{\sigma_x}{2}\cos(\alpha)$$

$$y = y_c - \frac{\sigma_y}{2}\sin(\alpha)$$

where x represents a two-dimensional vector, • represent vector dot product, $\kappa>1$ such that a region comprises the anatomy plus some margin, (1, 0) denotes the horizontal unit vector, $x_c=(x_c, y_c)$, and $\eta \in (0,1]$.

Figure 5:
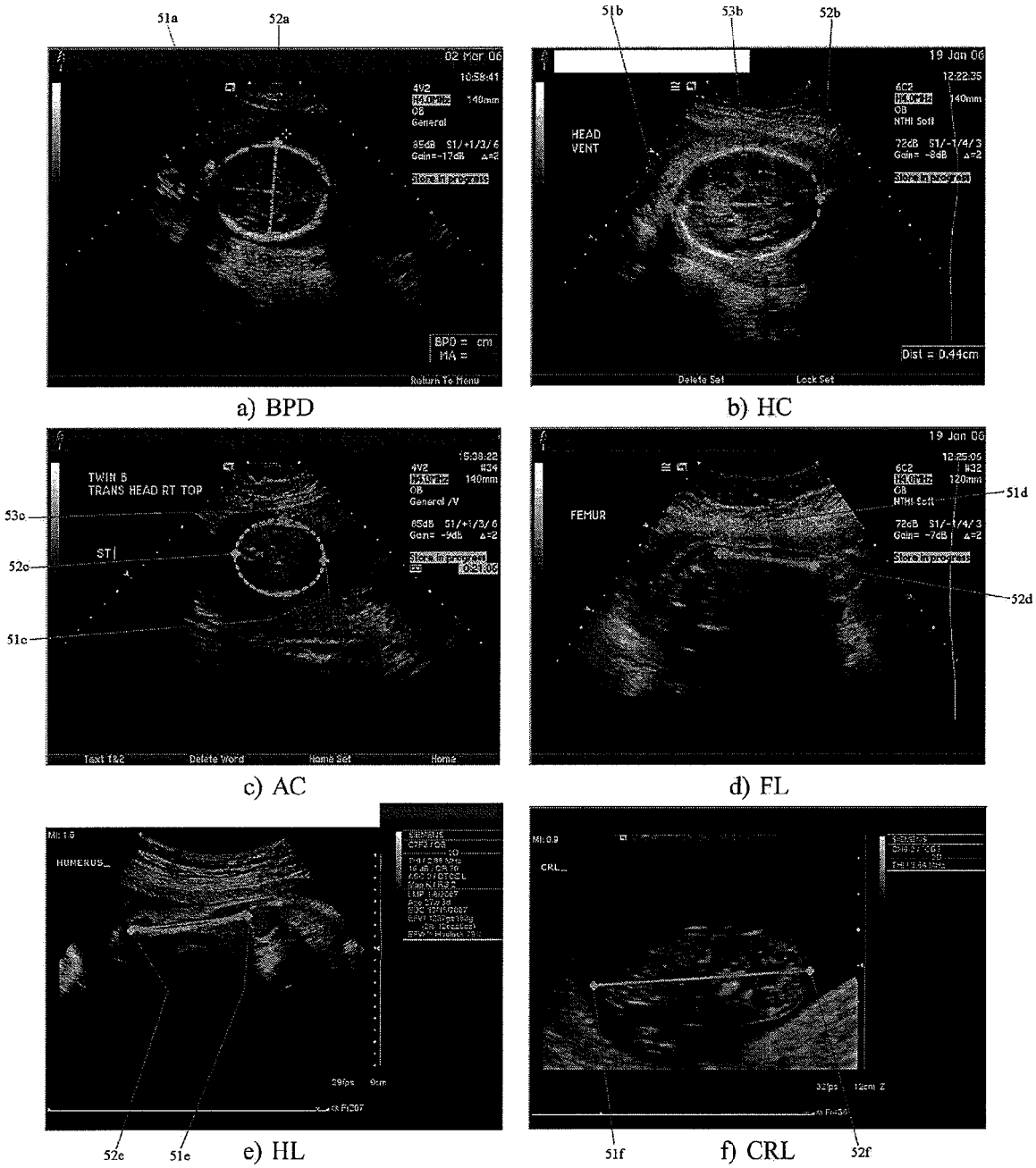
FIGS. 5(a)-(f) shows expert annotations for the BPD, HC, AC, FL, HL, and CRL measurements, according to an embodiment of the invention.
Figure 7:
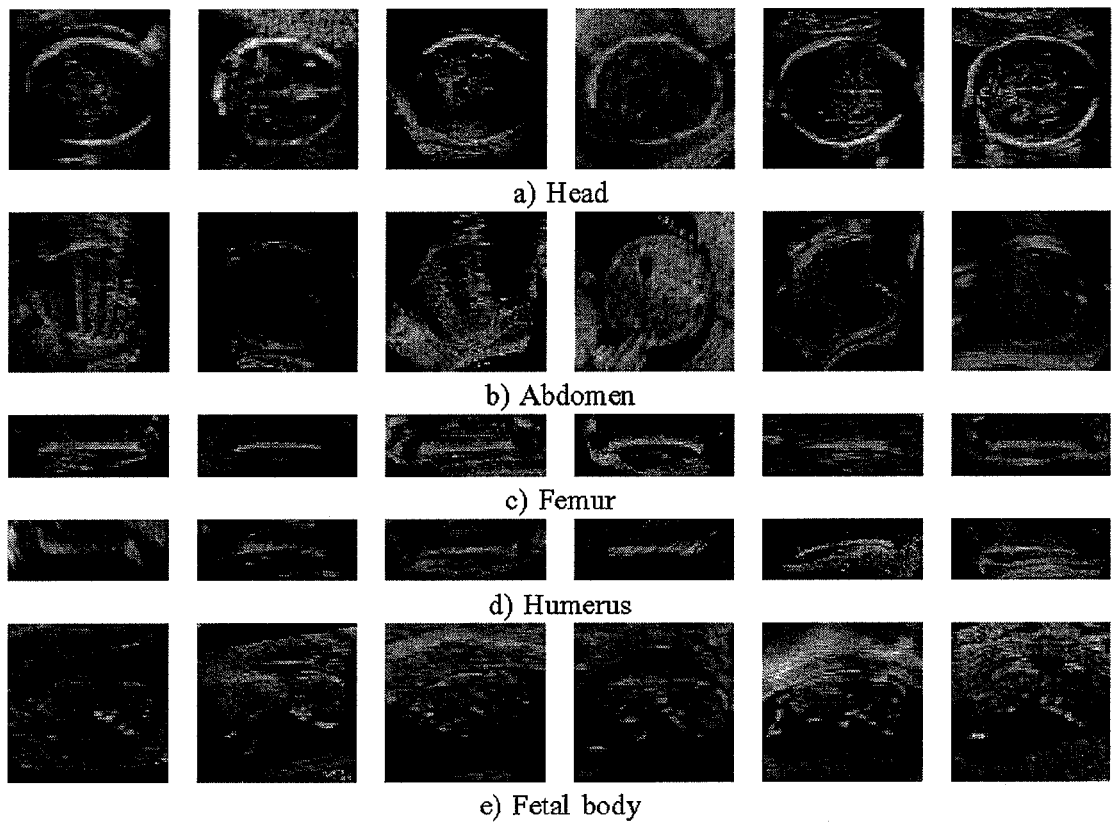
FIGS. 7(a)-(e) depicts examples of the training set for the BPD HC, AC, FL, HL, and CRL measurements, according to an embodiment of the invention.

The manual annotation is designed to provide aligned images of anatomies normalized in terms of orientation, position, scale, and aspect ratio. These images will be used for training the classifier. According to an embodiment of the invention, there are five classifiers to be trained: (1) head, (2) abdomen, (3) femur, (4) humerus, and (5) fetal body. The head classifier is used to provide the HC and BPD measurements (note that even though the BPD is a line measurement it is derived from the HC measurement through the use of its minor axis), the abdomen classifier allows for the AC, the femur classifier is used to produce the FL, the humerus classifier produces HL, and the fetal body is used to compute the CRL measurement. FIG. 5(b) shows a head annotation, where caliper 51b is located at the back of the head, caliper 52b is at the front of the head, and caliper 53b defines the minor axis of the ellipse and is located at the side of the head (moving from $x_1$ to $x_2$ in counter-clockwise direction). FIG. 5(a) shows the BPD annotation, respectively, where caliper 51a and 52a are interchangeably located at the end points of the minor axis of the head. FIG. 5(c) shows the abdomen annotation, where caliper 51c is located at the umbilical vein region, caliper 52c is at the spinal chord, and caliper 53c defines the minor axis of the ellipse and is located close to the stomach. FIGS. 5(d) and (e) display the femur and humerus annotations, respectively, where caliper 51d, 51e and 52d, 52e are interchangeably located at the end points of the femur bone. Finally, FIG. 5(f) displays the fetal body annotation, respectively, where caliper 51f is located at the bottom of the fetal body and 52f is located at the head. This annotation protocol allows for building an aligned training set. FIGS. 7(a)-(e) depicts examples of the training set for BPD and HC in FIG. 7(a), AC in FIG. 7(b), FL in FIG. 7(c), HL in FIG. 7(d), and CRL in FIG. 7(e), with $\kappa=1.5$ and $\eta=0.38$ for femur and humerus and $\eta=0.80$ for fetal body in EQS. (7) and (8). The values for $\eta$ are defined based on the aspect ratio of the anatomical structure. Notice that the original image regions are transformed into a square size of 78×78 pixels using linear interpolation in the cases of head, abdomen, and fetal body, and into a rectangular size of 78×30 pixels using bi-linear interpolation for femur and humerus with aspect ratio $$\frac{\text{width}}{\text{height}} = \frac{1}{\eta}$$

for $\eta=0.38$.

Training a Constrained Probabilistic Boosting Tree

Figure 9:
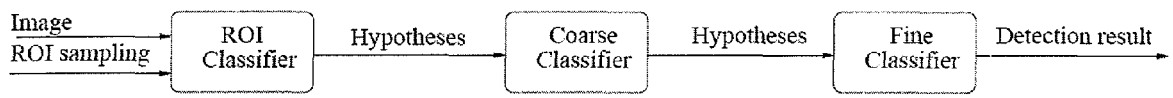
FIG. 9 is a flowchart of a training sequence according to an embodiment of the invention.

As mentioned above, the training involves a sequence of classification problems of increasing complexity. According to an embodiment of the invention, a training procedure involving three stages is used, where the three stages are referred to as the region of interest (ROI) classification stage, the coarse classification stage and the fine classification stage. A flowchart of a training sequence according to an embodiment of the invention is shown in FIG. 9.

Referring to the figure, the ROI classifier stage step 91 takes as input image samples from a region of interest (ROI). The ROI stage uses a subset of the initial parameter set to quickly detect a hypothesis for subsequent classification stages. Recall that the image is rotated in intervals of $\delta_\alpha$ and the integral image is computed for each rotated version of the image. During detection, determining the parameter $\alpha$ in EQ. (1) requires loading the respective rotated integral image, which is in general a time consuming task because it is not possible to have all integral images loaded in cache. A typical image size is 600×800 pixels, where each pixel is represented by a floating point number, which means that each image is about 2 MB. Therefore, leaving the parameter $\alpha$ out of the ROI classifier means a gain in terms of detection efficiency. Another observation for the ROI stage is that the aspect ratio $\sigma_x/\sigma_y$ of the anatomy does not vary significantly in the training set. Specifically, for heads, abdomens, and fetal body, $\sigma_x/\sigma_y \in [0.8,1.2]$, and for femurs and humerus, $\sigma_x/\sigma_y=1/\eta$. Therefore, the parameter $\sigma_y$ can also be omitted from the ROI stage, and its estimation occurs in the subsequent stages.

As a result, in the ROI stage, the positive samples are located in a region of the parameter space defined by:

$$\Delta_+^{ROI}=[\Delta_x^{ROI},\Delta_y^{ROI},X,\Delta_{\sigma_x}^{ROI},X], \quad (9)$$

where $$\Delta_x^{ROI} \in [x-\delta_x^{ROI}, x+\delta_x^{ROI}],$$

$$\Delta_y^{ROI} \in [y-\delta_y^{ROI}, y+\delta_y^{ROI}],$$

$$\Delta_{\sigma_x}^{ROI} \in [\sigma_x-\delta_{\sigma_x}^{ROI}, \sigma_x+\delta_{\sigma_x}^{ROI}],$$

and X denotes a parameter that is not learned in this stage, in this case $\sigma_y$ and $\alpha$. FIG. 4 illustrates this concept of training for a subset of the initial parameter set. Recall that the positive sample is located at $(x, y, \alpha, \sigma_x, \sigma_y)$ as defined in EQ. (1).

On the other hand, the negative samples are located in the following region of the parameter space:

$$\Delta_-^{ROI}=\Theta-\Delta_+^{ROI}, \quad (10)$$

where $\Theta$ represents the whole parameter space. The ROI classifier can detect the position and scale of the object, within the limits of $\Delta_+^{ROI}$, but not its rotation or its aspect ratio. That is, $\alpha=0$ and $\sigma_y=\sigma_x$ in EQS. (7) and (8) for this stage. This means that the training images are kept in their original orientation and aspect ratio, resulting in training images aligned only in terms of position and scale, and these images are transformed to a square patch of size 78×78 pixels. FIGS. 8(a)-(e) depicts some examples of the ROI training set for BPD and HC in FIG. 8(a), AC in FIG. 8(b), FL in FIG. 8(c), HL in FIG. 8(d), and CRL in FIG. 8(e).

Referring again to FIG. 9, the coarse classifier at step 92 is then trained with positive samples from the parameter subset:

$$\Delta_+^{coarse} = [\Delta_x^{coarse}, \Delta_y^{coarse}, \Delta_\alpha^{coarse}, \Delta_{\sigma_x}^{coarse}, \Delta_{\sigma_y}^{coarse}], \quad (11)$$

where $$\Delta_x^{coarse} \in [x - \delta_x^{coarse}, x + \delta_x^{coarse}],$$

$$\Delta_y^{coarse} \in [y - \delta_y^{coarse}, y + \delta_y^{coarse}],$$

$$\Delta_\alpha^{coarse} \in [\alpha - \delta_\alpha^{coarse}, \alpha + \delta_\alpha^{coarse}],$$

$$\Delta_{\sigma_x}^{coarse} \in [\sigma_x - \delta_{\sigma_x}^{coarse}, \sigma_x + \delta_{\sigma_x}^{coarse}],$$

$$\Delta_{\sigma_y}^{coarse} \in [\sigma_y - \delta_{\sigma_y}^{coarse}, \sigma_y + \delta_{\sigma_y}^{coarse}].$$

To improve the precision of the detection from the ROI to the coarse classifier, one sets $\delta^{coarse} < \delta^{ROI}$ in EQ. 9 for all parameters.

The negative samples for the coarse classifier are located in the following region of the parameter space:

$$\Delta_-^{coarse} = \Delta_-^{ROI} - \Delta_+^{coarse}, \quad (12)$$

where $\Delta_-^{ROI}$ is defined in EQ. (10).

Finally, the positive samples for the fine classifier, step 93 of FIG. 9, are within the subset:

$$\Delta_+^{fine} = [\Delta_x^{fine}, \Delta_y^{fine}, \Delta_\alpha^{fine}, \Delta_{\sigma_x}^{fine}, \Delta_{\sigma_y}^{fine}], \quad (13)$$

where $$\Delta_x^{fine} \in [x - \delta_x^{fine}, x + \delta_x^{fine}],$$

$$\Delta_y^{fine} \in [y - \delta_y^{fine}, y + \delta_y^{fine}],$$

$$\Delta_\alpha^{fine} \in [\alpha - \delta_\alpha^{fine}, \alpha + \delta_\alpha^{fine}],$$

$$\Delta_{\sigma_x}^{fine} \in [\sigma_x - \delta_{\sigma_x}^{fine}, \sigma_x + \delta_{\sigma_x}^{fine}],$$

$$\Delta_{\sigma_y}^{fine} \in [\sigma_y - \delta_{\sigma_y}^{fine}, \sigma_y + \delta_{\sigma_y}^{fine}].$$

The detection precision from the coarse to the fine classifier is improved by setting $\delta^{fine} < \delta^{coarse}$ in EQ. (11) for all parameters.

The negative samples for the fine classifier are located in the following region of the parameter space:

$$\Delta_-^{fine} = \Delta_-^{coarse} - \Delta_+^{fine}, \quad (14)$$

where $\Delta_-^{coarse}$ is defined in EQ. (12).

A training algorithm according to an embodiment of the invention is as follows.

Data: Set of M training images with respective parameter of
the region containing the anatomy $\{(I, \theta)_i\}$, $i=1,...,M$;
    Maximum height $H_{ROI}$ of the ROI classifier tree and
total number of nodes $N_{ROI}$;
    Maximum height $H_{coarse}$ of the Coarse classifier tree and
total number of nodes $N_{coarse}$;
    Maximum height $H_{fine}$ of the Fine classifier tree and
total number of nodes $N_{fine}$;
    $I^+ = \emptyset$ and $I^- = \emptyset$;
    for i = 1,...,M do
        Generate P positive samples by randomly sampling the
parameter sub-space $\Delta_+^{ROI}$ and add these samples to the set of
positive samples $I^+$
        Generate N negative samples by randomly sampling the
parameter sub-space $\Delta_-^{ROI}$ and add these samples to the set of
negative samples $I^-$
    end
    Train ROI classifier of height $H_{ROI}$ and number of nodes $N_{ROI}$
using $I^+$ and $I^-$.
    $I^+ = \emptyset$ and $I^- = \emptyset$;
    for i = 1,...,M do
        Generate P positive samples by randomly sampling the
parameter sub-space $\Delta_+^{coarse}$ and add these samples to the set of
positive samples $I^+$
        Generate N negative samples by randomly sampling the
parameter sub-space $\Delta_-^{coarse}$ and add these samples to the set of
negative samples $I^-$
    end
    Train coarse classifier of height $H_{coarse}$ and number of nodes
$N_{coarse}$ using $I^+$ and $I^-$.
    $I^+ = \emptyset$ and $I^- = \emptyset$;
    for i = 1,...,M do
        Generate P positive samples by randomly sampling the
parameter sub-space $\Delta_+^{fine}$ and add these samples to the set of
positive samples $I^+$
        Generate N negative samples by randomly sampling the
parameter sub-space $\Delta_-^{fine}$ and add these samples to the set of
negative samples $I^-$
    end
    Train fine classifier of height $H_{fine}$ and number of nodes
$N_{fine}$ using $I^+$ and $I^-$.
    Result: ROI, coarse, and fine classifiers.

Detection

According to a training algorithm according to an embodiment of the invention, the detection algorithm runs in three stages. The ROI detection samples the search space uniformly using the $\delta_{\{x,y,\sigma_x\}}^{ROI}$ as the sampling interval for position and scale. The coarse detection only classifies the positive samples for the ROI detector at smaller intervals of $\delta_{\{x,y,\alpha,\sigma_x,\sigma di\ y\}}^{coarse}$, while the fine detection searches the hypotheses selected from the coarse search at smaller intervals of $\delta_{\{x,y,\alpha,\sigma_x,\sigma_y\}}^{fine}$.

A detection algorithm according to an embodiment of the invention is as follows.

Data: Test image and measurement to be performed (BPD, HC,
AC, FL, HL, or CRL);
    ROI, coarse, and fine classifiers;
    $H_{ROI} = \emptyset$;
for $\theta = [0,0,0,0,0]$: $\delta_{ROI}$: $[\max(x), \max(y), 0, \max(\sigma_x), 0]$ do
    $\sigma_y = \sigma_x$;
    Compute $P(y=+1|S)$ using ROI classifier, where S is an image
region determined by $\theta$;
    $H_{ROI} = H_{ROI} \cup (\theta, P(y = +1|S))$
end
Assign all hypotheses from $H_{ROI}$ in terms of $P(y=+1|S)$ to $H_{coarse}$
for i = 1,..., $|H_{coarse}|$ do
    Assume $(\theta_i, P_i) = 1^{th}$ element of $H_{coarse}$ $$\text{for } \theta = [x_i - \delta_x^{ROI}, y_i - \delta_y^{ROI}, 0, \sigma_{x,i} - \delta_{\sigma_x}^{ROI}, 0]: \delta_{course}: \\ [x_i + \delta_x^{ROI}, y_i + \delta_y^{ROI}, \max(\alpha), \sigma_{x,i} + \delta_{\sigma_x}^{ROI}, \max(\sigma_y)] \text{ do}$$

-continued

```
        Compute P(y = +1|S) using coarse classifier, where S is an
        image region determined by θ
            H_coarse = H_coarse ∪ (θ,P(y = +1|S))
        end
    end
    Assign the top H hypotheses from H_coarse in terms of P(y=+1|S) to H_fine
    for i = 1,..., |H_fine| do
        Assume (θ_i, P_i) = i^th element of H_fine for θ = (θ_i − δ^coarse_{x,y,α,σ_x,σ_y}): δ^fine_{x,y,α,σ_x,σ_y}: (θ_i − δ^coarse_{x,y,α,σ_x,σ_y}) do Compute P(y=+1|S) using fine classifier, where S is an image
            region determined by θ
                H_fine = H_fine ∪ (θ,P(y = +1|S))
        end
    end
    Select the top hypothesis from H_fine in terms of P(y=+1|S), display
    hypothesis if P(y=+1|S)> τ_DET
    Result: Parameter θ of the top hypothesis.
```

The value $\tau_{DET}$ was set in order to eliminate the bottom 5% of the cases in the training set. Setting such threshold helps to avoid large error cases. Therefore, after the detection process, if $P(y=+1|S)<\tau_{DET}$, then the system can output a message indicating that no anatomy was detected.

Training Results

There were 1,426 expert annotated training samples for head, 1,293 for abdomen, 1,168 for femur, 547 for humerus, and 325 for fetal body available for training an ROI, a coarse, and a fine CPBT classifiers. A goal is to determine a tree structure of the classifier, where the tree is constrained to have the fewest possible number of nodes without affecting the classifier performance. Recall that a smaller number of nodes produces more efficient training and detection processes and a more generalizable classifier. Therefore, the performance of the full binary tree is compared against a tree constrained to have only one child per node. The number of weak classifiers is set to be at most 30 for the root node and its children (i.e., nodes at heights 0 and 1), and at most 30×(tree height) for the remaining nodes. Note that the actual number of weak classifiers is automatically determined by the AdaBoost algorithm. The height of each tree is defined as $H_{ROI} \in [1, 7]$, $H_{coarse} \in [1, 10]$, and $H_{fine} \in [1, 15]$, with its specific value determined through the following stop condition: a node cannot be trained with less than 2,000 positive and 2,000 negative samples, for a total of 4,000 samples. This stop condition basically avoids over-fitting of the training data. The sampling intervals values for each stage are $\delta_{ROI}=[15, 15, X, 15, X]$, $\delta_{coarse}=[8, 8, 20°, 8, 8]$, and $\delta_{fine}=[4, 4, 10°, 4, 4]$. Finally, in a training algorithm according to an embodiment of the invention, the number of additional positives per image is P=100 and the number of negatives per image is N=1000.

From the parameter $\theta=[x, y, \alpha, \sigma_x, \sigma_y]$ of the top hypothesis, each measurement can be computed as follows.

BPD=$\gamma\sigma_y$, using the response from the head detector, where $\gamma=0.95$. This value for $\gamma$ is estimated from the training set by computing $$\gamma = \frac{1}{M}\sum_{i=1}^{M}\frac{BPD(i)}{2r_y(i)}$$

with M being the number of training images for heads, BPD(i) is the manual BPD measurement for image i, $$r_y(i) = \frac{\sigma_y(i)}{2\kappa}$$

with $\sigma_y(i)$ denoting the height of the rectangle which contains the head image i (see EQ. (7)).

HC=$\pi\lfloor 3(r_x+r_y)-\sqrt{(3r_x+r_y)(r_x+3r_y)}\rfloor$, where this value is the Ramanujan's approximation of the ellipse circumference with $$r_x = \frac{\sigma_x}{2\kappa} \text{ and } r_y = \frac{\sigma_y}{2\kappa}$$

(see EQ. (7)).

AC=$\pi\lfloor 3(r_x+r_y)-\sqrt{(3r_x+r_y)(r_x+3r_y)}\rfloor$, which is the same computation as for HC.

FL, HL, CRL=$2r_x$, where $$r_x = \frac{\sigma_x}{2\kappa}$$

(see EQ. 8).

Figure 10:
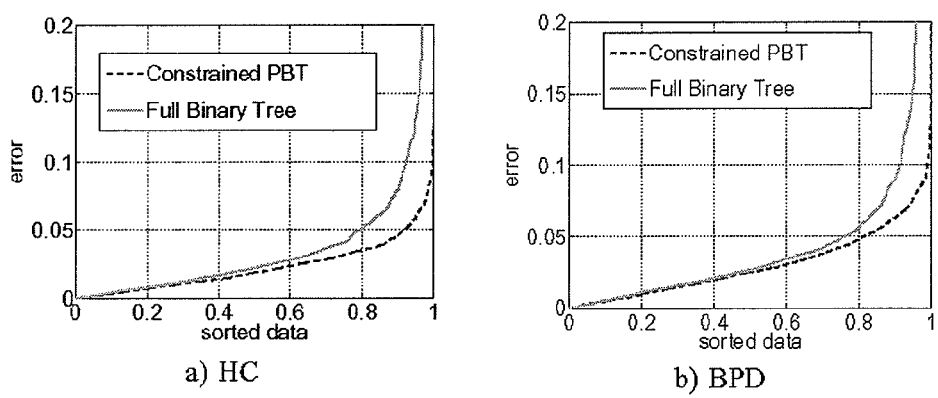
FIGS. 10(a)-(b) shows the measurement errors for HC and BPD in the training set for the constrained tree and the full binary tree, according to an embodiment of the invention.
Figure 8:
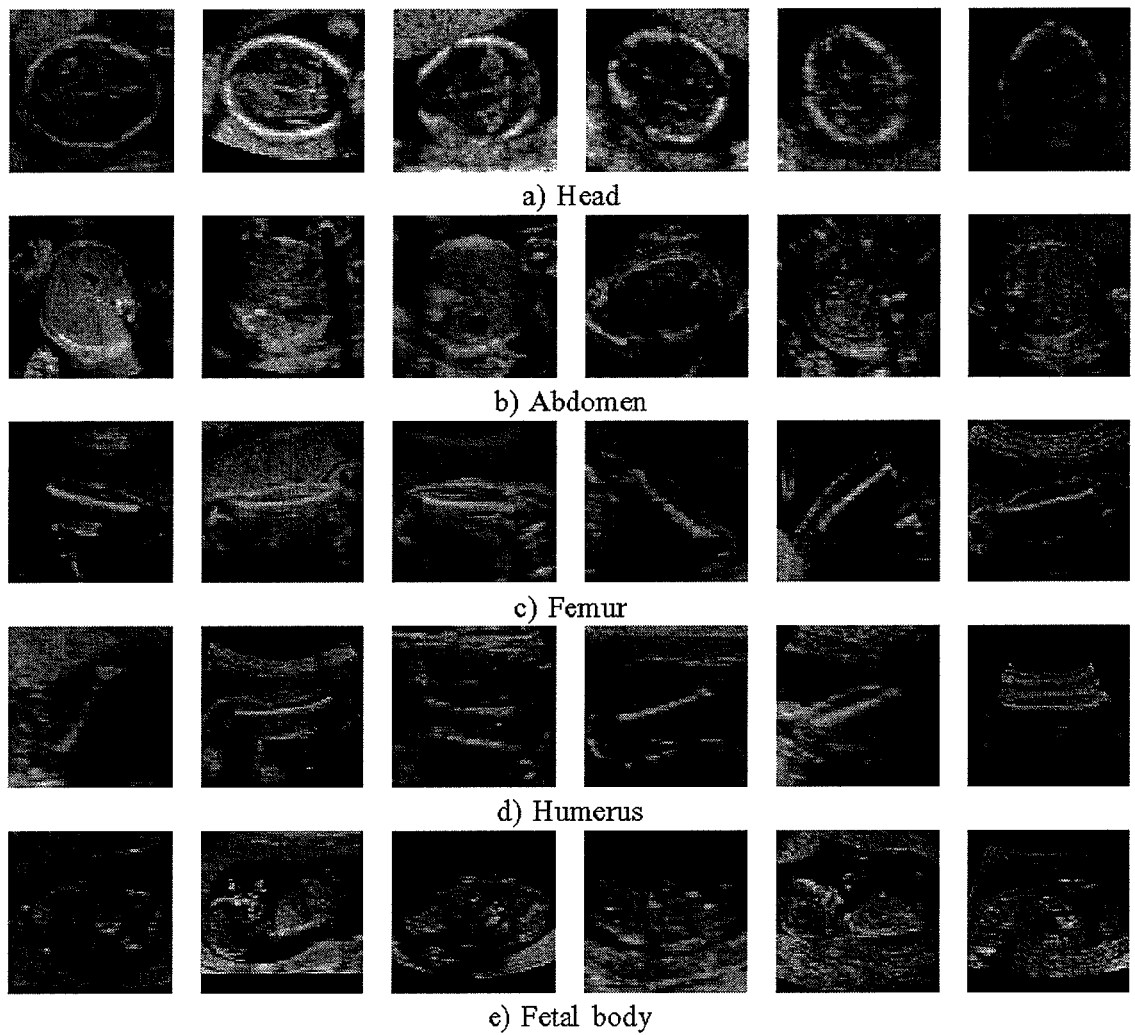
FIGS. 8(a)-(e) depicts some examples of the ROI training set for BPD HC, AC, FL, HL, and CRL measurements, according to an embodiment of the invention.

FIGS. 10(a)-(b) shows the measurement errors for HC and BPD in the training set for the constrained tree and the full binary tree, where the training cases are sorted in terms of the error value. The horizontal axes show the training set indices, which varies from 0 to 1, where 0 is the index to the training case with the smallest error, and 1 represents the case with the largest error. Assuming that GT contains the expert annotation for BPD, HC, AC, FL, HL, or CRL and DT denotes the respective automatic measurement produced by the system, the error is computed as:

$$\text{error}=|GT-DT|/GT. \quad (15)$$

Notice that the performance of the constrained tree is better than that of the full binary tree. This is explained by the fact that the constrained tree is more regularized and should be able to generalize better than the full binary tree. Another feature of the constrained tree is the efficiency in training and testing. For the cases above, the training process for the full binary tree takes between seven to ten days, while that for the constrained tree takes two to four days on a standard PC computer. A detection process according to an embodiment of the invention for the constrained tree takes, on average, less than one second, while that of the full binary tree takes around three to four seconds.

Experimental Assessment Methodology

For a quantitative assessment of an algorithm according to an embodiment of the invention, a methodology proposed by V. Chalana and Y. Kim, "A methodology for evaluation of boundary detection algorithms on medical images", *IEEE Transactions on Medical Imaging*, 16 (5), pp. 642-652, 1997, and revised by C. Lopez, M. Fernandez, and J. Alzola, "Comments on: A methodology for evaluation of boundary detection algorithms on medical images", *IEEE Transaction on Medical Imaging*, 23 (5), pp. 658-660, 2004, the contents of both of which are herein incorporated by reference, was used. This methodology will be explained as follows.

Assume that the segmentation of the anatomy is produced by a curve $A=\{a_1, \ldots, a_m\}$, where $a_i \in R^2$ represent the image positions of the m control points that define this curve. Given another curve $B=\{b_1, \ldots, b_m\}$, the Hausdorff distance between these two curves is defined by $$e(A,B)=\max(\max_i\{d(a_i,B)\},\max_j\{d(b_j,A)\}), \quad (16)$$

where $d(a_i, B) = \min_j \|b_j - a_i\|$, with $\|\ \|$ denoting Euclidean distance.

The gold standard measurement is obtained through the average of the user observations. Given that $GT_{(i,j)}$ represents the measurement of user $i \in \{1, \ldots, n\}$ on image $j \in \{1, \ldots, N\}$ (i.e., GT represents one of the six measurements considered herein: BPD, HC, AC, FL, HL, CRL), then the gold standard measurement for image j is obtained as:

$$\overline{GT_j} = \frac{1}{n}\sum_{i=1}^{n} GT_{(i,j)}. \tag{17}$$

The following statistical evaluations compare the computer-generated segmentation to the multiple observers' segmentations. The main goal of these evaluations is to verify whether the computer-generated segmentations differ from the manual segmentations as much as the manual segmentations differ from one another. Assume that there is a database of curves, such as A and B in EQ. (16), represented by the variable $x_{i,j}$, with $i \in \{0, \ldots, n\}$ and $j \in 1, \ldots, N$, where i is a user index and j is an image index. User i=0 represents the computer-generated curve, while users $i \in \{1, \ldots, n\}$ are the curves defined from the manual segmentations. The following two kinds of evaluations are used: (1) a modified Williams index; and (2) a percentage statistic. The modified Williams index is defined as:

$$I' = \frac{\frac{1}{n}\sum_{j=1}^{n}\frac{1}{D_{0,j}}}{\frac{2}{n(n-1)}\sum_{j}\sum_{j':j'\neq j}\frac{1}{D_{j,j'}}}, \tag{18}$$

where $$D_{j,j'} = \frac{1}{N}\sum_{i=1}^{N} e(x_{i,j}, x_{i,j'})$$

with $e(,)$ defined in EQ. (16). A confidence interval (CI) is estimated using a jackknife non-parametric sampling technique as follows:

$$I'_{()} = \pm z_{0.95} se, \tag{19}$$

where $Z_{0.95} = 1.96$, representing the 95th percentile of the standard normal distribution, $$se = \left\{\frac{1}{N-1}\sum_{i=1}^{N}[I'_{(i)} - I'_{()}]\right\}^2$$

with $$I'_{()} = \frac{1}{N}\sum_{i=1}^{N} I'_{(i)}.$$

Note that $I'_{(i)}$ is the Williams index of EQ. (18) calculated by leaving image i out of the computation of $D_{jj'}$. A successful measurement for the Williams index is to have $I'_{()}$ close to 1.

The percentage statistic transforms the computer-generated and manual curves into points in a 2m-dimensional Euclidean space (recall from EQ. (16) that m is the number of control points of the segmentation curve), and the goal is to verify the percentage of times the computer-generated curve is within the convex hull formed by the manual curves. An approximation to this measure is $$\max_i \{e(C, O_i)\} \leq \max_{i,j}\{e(O_i, O_j)\}, \tag{20}$$

where C is the computer-generated curve, $O_i$ for $i \in \{1, \ldots, n\}$ are the observer-generated curves, and $e(,)$ defined in EQ. (16). The expected value for the percentage statistic depends on the number of observer-generated curves. A successful expected value for the confidence interval of EQ. (20) should be greater than or equal to $$\frac{n-1}{n+1},$$

where n is the number of manual curves. The confidence interval for EQ. (20) is computed in the same way as in EQ. (19).

Experimental Protocol

An algorithm according to an embodiment of the invention was quantitatively evaluated in a clinical setting using typical ultrasound examination images. All ultrasound images used in this evaluation were not included in the training set. The evaluation protocol was set up as follows.

(1) A user selects an ultrasound image of a fetal head, abdomen, femur, humerus, or fetal body.

(2) The user presses the relevant detection button (i.e., BPD or HC for head, AC for abdomen, FL for femur, HL for humerus, CRL for fetal body).

(3) The system displays automatic detection and measurement and saves the computer-generated curve.

(4) The user makes corrections to the automatic detection and saves the manual curve.

Three sets of data are available, as follows:

Set 1: 10 distinct images of fetal heads, 10 distinct images of fetal abdomen, and 10 distinct images of fetal femur were evaluated by five expert users. Therefore, there are five different manual measurements per image, for a total of 40×5=200 measurements.

Set 2: Expert user 1 annotated 59 head images, 53 abdomen images, and 50 femur images. Expert user 2 annotated 59 head images, 53 abdomen images, and 50 femur images. Expert user 3 annotated 59 head images, 53 abdomen images, and 50 femur images. Expert user 4 annotated 60 head images, 53 abdomen images, and 49 femur images. Expert user 5 annotated 60 head images, 53 abdomen images, and 49 femur images. In total, there are 297 head images, 265 abdomen images, and 248 femur images, which means that there is no overlap between images annotated by different users in this second set.

Set 3: Expert user 1 annotated 30 humerus and 35 fetal body images, Expert user 2 annotated 30 humerus and 35 fetal body images, Expert user 3 annotated 30 humerus and 35 fetal body images. In total, there are 90 humerus images, and 105 fetal body images, which means that there is no overlap between images annotated by different users in this third set.

Results

Figure 12:
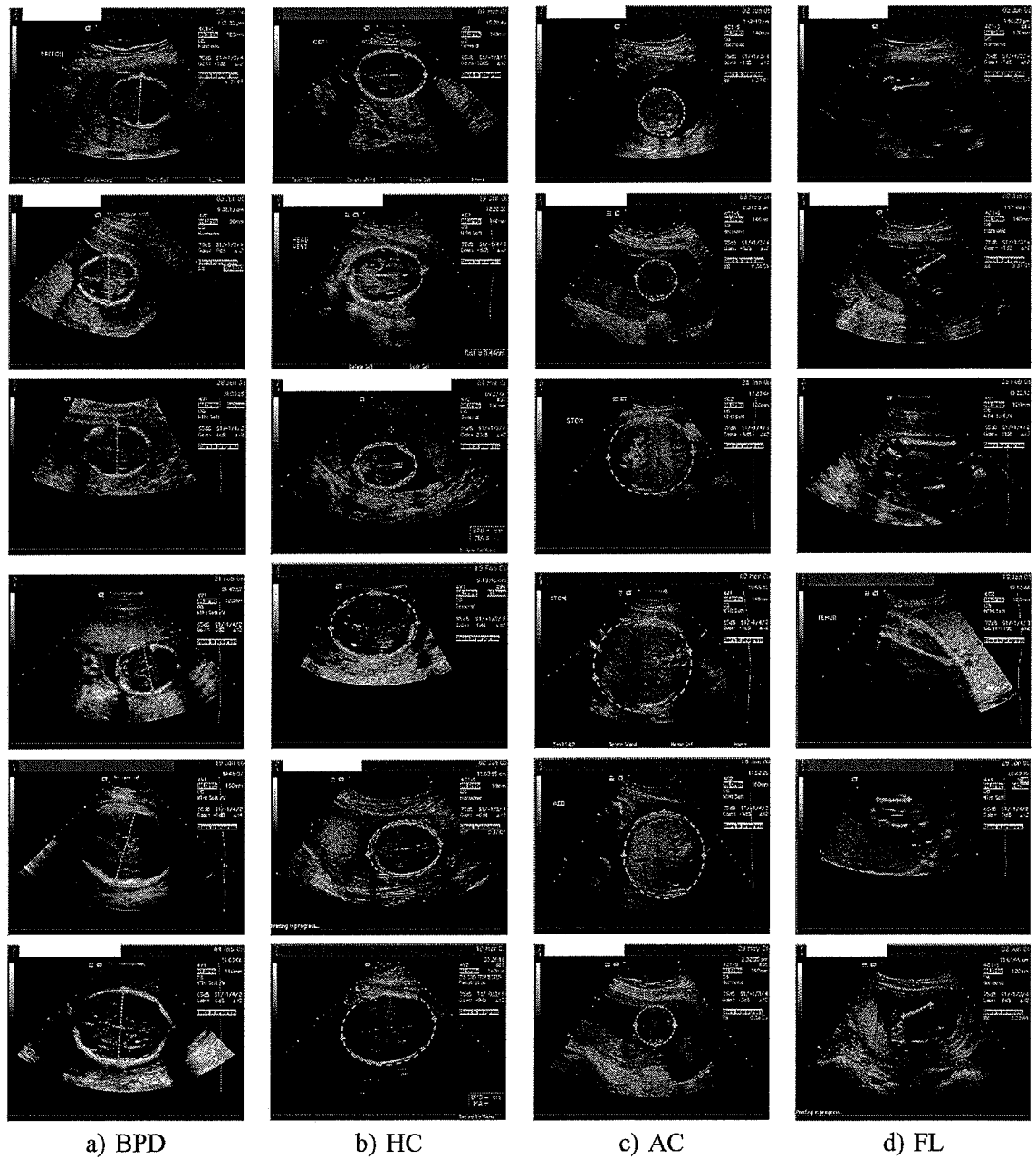
FIGS. 12(a)-(d) depicts detection and segmentation results for the BPD, HC, AC, and FL measurements, according to an embodiment of the invention.
Figure 13:
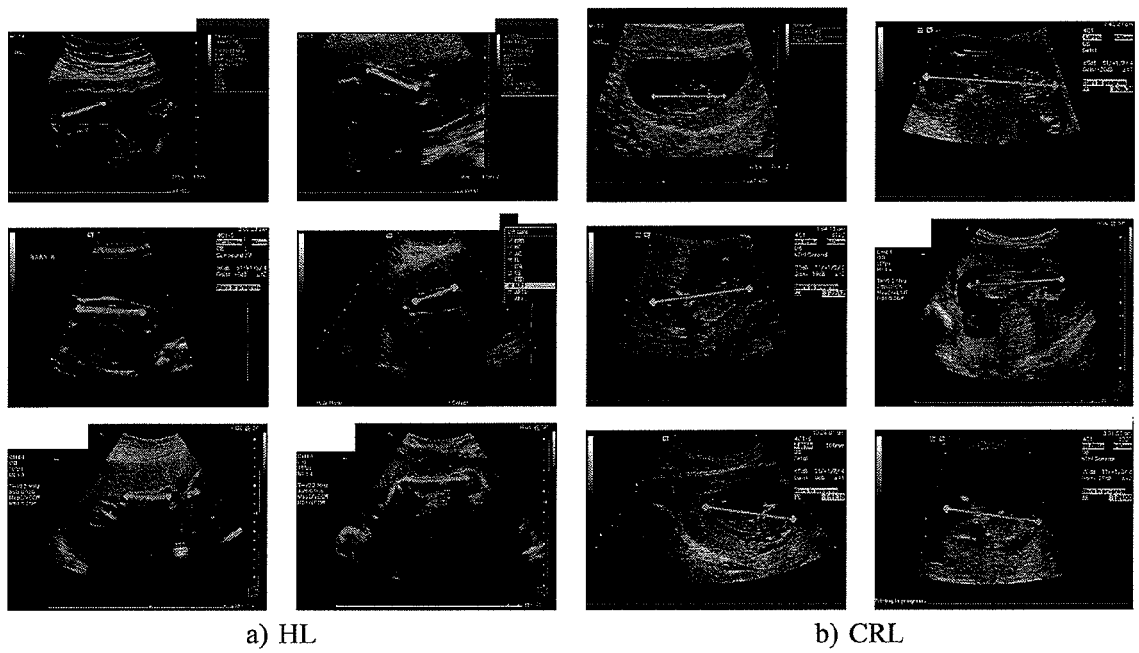
FIGS. 13(a)-(b) depicts detection and segmentation results for the HL and CRL measurements, according to an embodiment of the invention.

Qualitative results are shown in FIGS. 12-13 and the quantitative assessment of a system according to an embodiment of the invention using the Williams index and the percentage statistic described above.

Tables I and II, in FIGS. 14 and 15, respectively, show the error between control points of the curves generated by this system and by the manual measurements. Table I shows the comparison results of the computer generated curves to the five observers' curves for fetal skull, abdomen, and femur detections. In the table, CO is the mean computer-to-observer distance, IO is the mean inter-observer distance, WI is the Williams index, and CI is the confidence interval. The columns labeled SET 1 show the results for Set 1, and the columns labeled SET 2 show the results for Set 2. The curves generated for the HC and AC measurements contain 16 control points, while the curve for BPD, FL, HL, and CRL have two control points (just the end points of the line). Table II shows the comparison results of the computer generated curves to the five observers' curves for the fetal humerus and body detections for Set 3.

In addition to the Hausdorff distance, results using the average distance are also shown, where e(,) in EQ. (16) is substituted for $$e(A, B) = \frac{1}{2}\left(\frac{1}{m}\sum_{i=1}^{N} d(a_i, B) + \frac{1}{m}\sum_{j=1}^{M} d(b_j, A)\right)$$

for curves A and B. The Williams index and its confidence interval are shown in Table I for Set 1. The computer-to-observer errors measured on Sets 2 and 3 are displayed in Tables I (last column) and Table II, respectively. The Williams index could not be computed for Sets 2 and 3 because there were only one user measurement per image. Recall that the confidence interval for the Williams index has to be close to 1, so that it can be concluded that there is negligible statistical difference between the computer-generated and user measurements.

The measurement errors computed from Set 1 are shown in Table III, depicted in FIG. 15, which shows the comparison results of the computer generated curves to the gold-standard using absolute differences on Set 1. Note that this table only considered the errors of EQ. (15) computed from the measurements of BPD, HC, AC, and FL, and the gold-standard is obtained from the average of the five observers' measurements. The correlation coefficient r is also presented, which denotes the Pearson correlation, defined as follows:

$$r = \frac{\sum_i \sum_j GT_i DT_j - \frac{\sum_i GT_i \sum_j DT_j}{\# \text{ images}}}{\sqrt{\left(\sum_i GT_i^2 - \frac{(\sum_i GT_i)^2}{\# \text{ images}}\right)\left(\sum_i DT_i^2 - \frac{(\sum_i DT_i)^2}{\# \text{ images}}\right)}}, \quad (21)$$

where $GT_i$ is the user measurement and $DT_i$ is the system measurement for the $i^{th}$ image. The measurement errors computed from Sets 2 and 3 are shown in Table IV, presented in FIG. 16, which shows the comparison results of computer-generated measurements to the gold-standard using absolute differences for Set 2, where r=correlation coefficient and the gold-standard is simply the user measurement.

Figure 11:
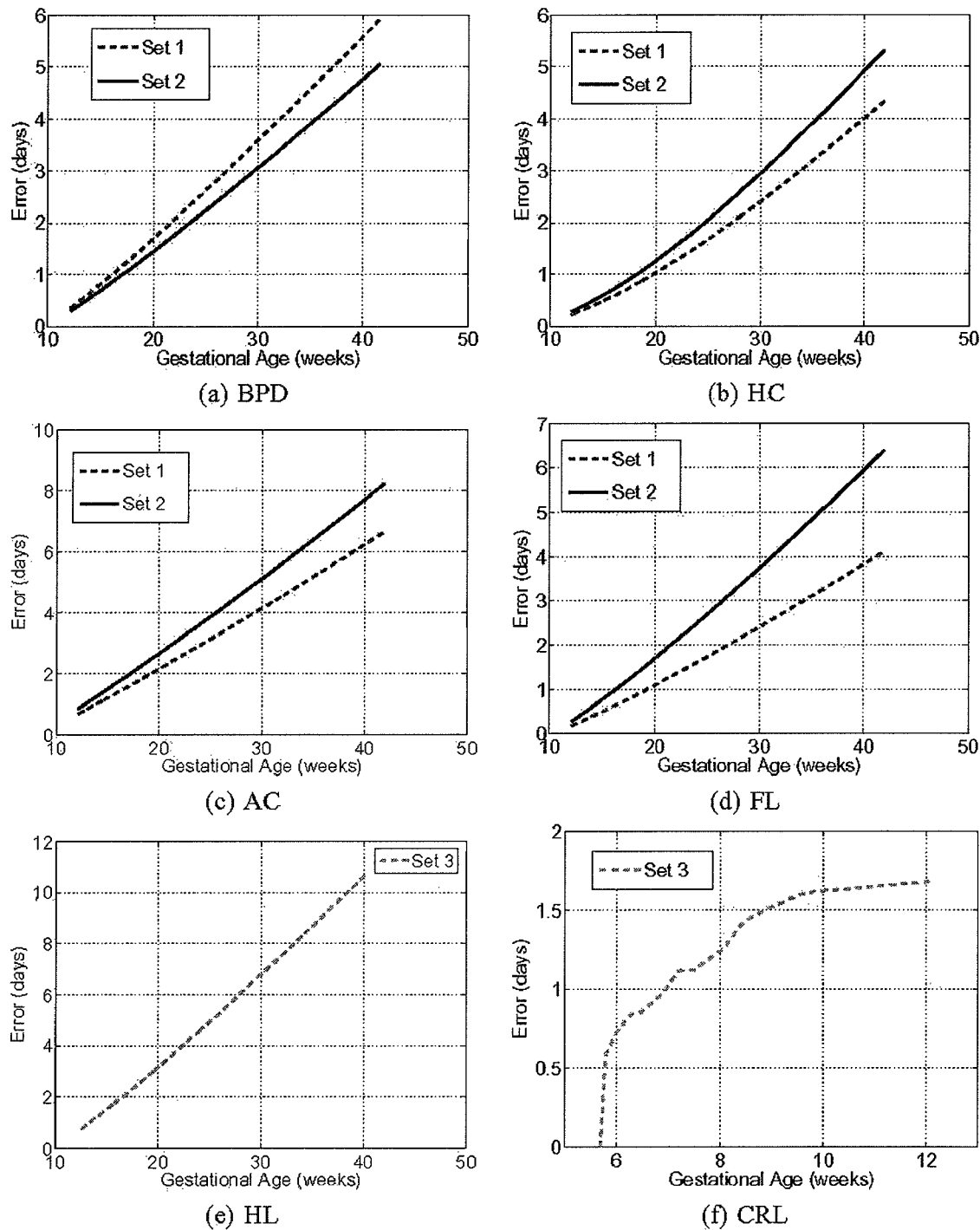
FIGS. 11(a)-(f) shows the average error in terms of days as a function of the gestational age of the fetus for the BPD, HC, AC, FL, HL, and CRL measurements, according to an embodiment of the invention.

Table V, presented in FIG. 16, shows the Williams index and percentage statistic with respect to the user measurements for BPD, HC, AC, and FL measurements on Set 1, where WI=Williams index, P=percent statistic, and CI=confidence interval. Note that the confidence interval for the percentage statistic should be around $$\frac{n-1}{n+1} = \frac{4}{6} = 0.66,$$

where n=5=number of manual measurements. Finally, FIGS. 11(*a*)-(*f*) shows the average error in terms of days as a function of the gestational age (GA) of the fetus for Sets 1, 2, and 3, for the BPD, HC, AC, FL, HL, and CRL measurements. In this case the gestational age is computed as a function of each measurement using the Hadlock regression function. The error is computed by taking the average error of the measurement (Table III for Set 1, and Table IV for Sets 2 and 3) and computing what that error represents in terms of number of days, but notice that this error varies as a function of the GA of the fetus.

For all cases above, notice that the confidence interval (CI) for the Williams index is around 1 for all measurements, and the percentage statistic CI is close to the expected value of 0.66 for all measurements. The AC measurement shows a result slightly below this mark, but given that the Williams index result for AC and for the abdomen curve is always close to one, it is fair to say that AC is producing acceptable results. In general, the HL and CRL measurements present similar results compared to the other anatomies, even though their classifier models were built with much smaller training sets. Finally, it is interesting to see in FIG. 11 that the errors reported for each anatomy represent a deviation of only a couple of days when GA<30 weeks and a few days (usually less than seven days) for GA>30 weeks.

The running time for an algorithm according to an embodiment of the invention is on average 0.5 seconds for all measurements on a PC computer with the following configuration: Intel Core 2 CPU 6600 at 2.4 GHz, 2 GB of RAM.

Additional results on previously unseen images are presented in FIGS. 12-13. FIGS. 12(*a*)-(*d*) depicts detection and segmentation results for the following measurements: BPD in FIG. 12(*a*); HC in FIG. 12(*b*); AC in FIG. 12(*c*); and FL in FIG. 12(*d*). FIGS. 13(*a*)-(*b*) depicts detection and segmentation results for the HL in FIG. 13(*a*) and CRL in FIG. 13(*b*).

System Implementations

It is to be understood that embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 17:
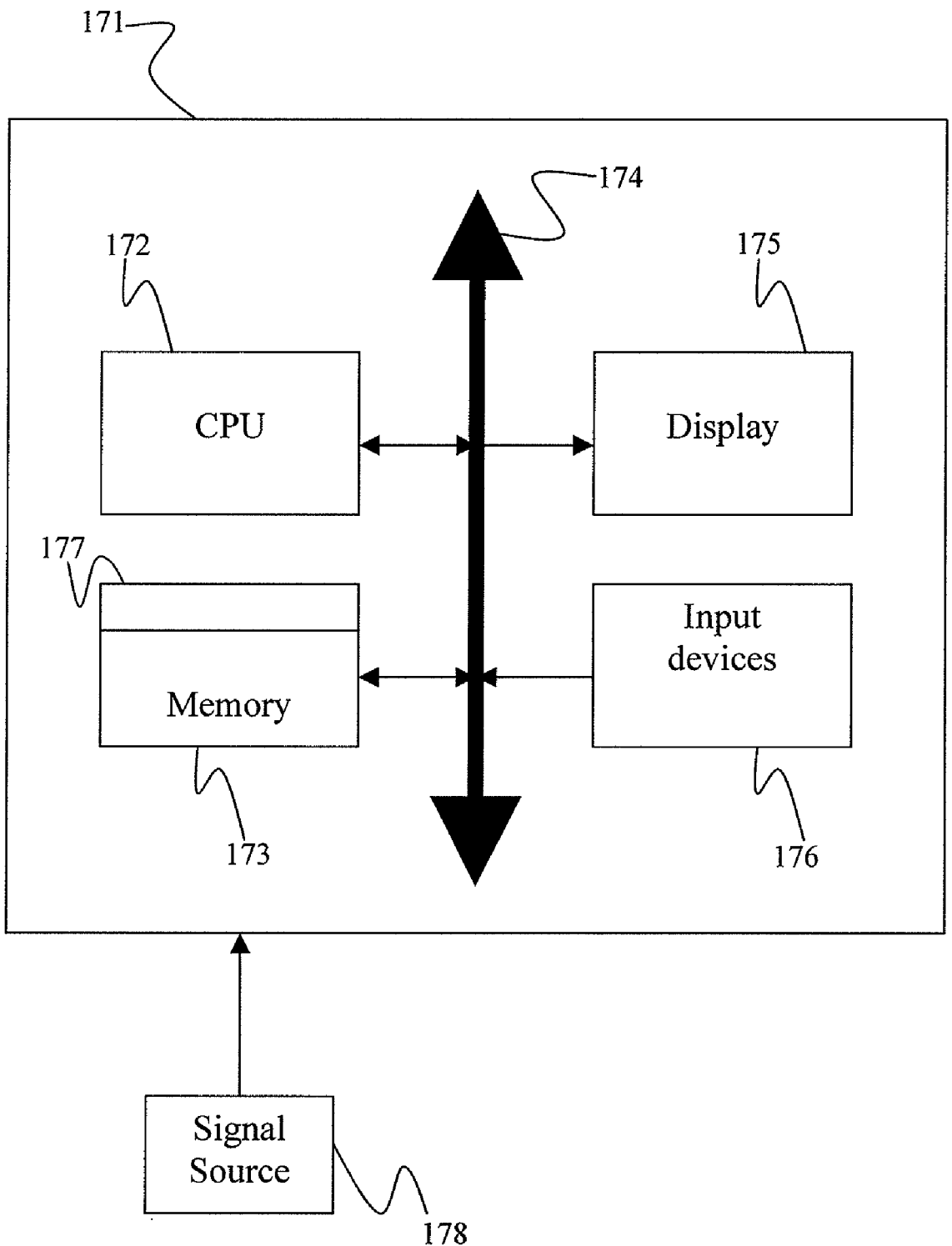
FIG. 17 is a block diagram of an exemplary computer system for implementing a method for the automatic detection and measurement of fetal anatomical structures in ultrasound images, according to an embodiment of the invention.

FIG. 17 is a block diagram of an exemplary computer system for implementing a method for the automatic detection and measurement of fetal anatomical structures in ultrasound images according to an embodiment of the invention. Referring now to FIG. 17, a computer system 171 for implementing the present invention can comprise, inter alia, a central processing unit (CPU) 172, a memory 173 and an input/output (I/O) interface 174. The computer system 171 is generally coupled through the I/O interface 174 to a display 175 and various input devices 176 such as a mouse and a keyboard. The support circuits can include circuits such as cache, power supplies, clock circuits, and a communication bus. The memory 173 can include random access memory (RAM), read only memory (ROM), disk drive, tape drive, etc., or a combinations thereof. The present invention can be implemented as a routine 177 that is stored in memory 173 and executed by the CPU 172 to process the signal from the signal source 178. As such, the computer system 171 is a general purpose computer system that becomes a specific purpose computer system when executing the routine 177 of the present invention.

The computer system 171 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that, because some of the constituent system components and method steps depicted in the accompanying figures can be implemented in software, the actual connections between the systems components (or the process steps) may differ depending upon the manner in which the present invention is programmed. Given the teachings of the present invention provided herein, one of ordinary skill in the related art will be able to contemplate these and similar implementations or configurations of the present invention.

While the present invention has been described in detail with reference to a preferred embodiment, those skilled in the art will appreciate that various modifications and substitutions can be made thereto without departing from the spirit and scope of the invention as set forth in the appended claims.

What is claimed is:

1. A method for detecting fetal anatomic features in ultrasound images, said method comprising the steps of:
    providing a plurality of ultrasound images of a fetus, each said image comprising a plurality of intensities associated with a 2-dimensional grid;
    providing a parameter vector specifying a region of interest S containing an anatomic feature of interest for each of said plurality of images;
    training a sequence of probabilistic boosting tree classifiers, each with a pre-specified height and number of nodes, wherein each classifier is trained with a set of positive feature samples and a set of negative feature samples generated for each of said plurality of images by randomly sampling a parameter subspace, wherein each classifier computes a posterior probability $P(y|S)$ where $y \in \{-1,+1\}$, with $P(y=+1|S)$ representing a probability that the image region S contains the feature of interest, and $P(y=-1|S)$ representing a probability that image region S contains background information; and
    detecting said anatomic feature of interest in a new ultrasound image using said probabilistic boosting tree classifiers.

2. The method of claim 1, wherein each region of interest (ROI) S is determined by parameter vector $\theta = [x, y, \alpha, \sigma_x, \sigma_y]$, wherein (x, y) represent a top left position in said ROI, $\alpha$ denotes an orientation of said ROI, and $(\sigma_x, \sigma_y)$ represent a scale of said ROI.

3. The method of claim 2, wherein said sequence of probabilistic boosting tree classifiers comprises an ROI classifier, a coarse classifier, and a fine classifier.

4. The method of claim 3, wherein said ROI classifier is trained on positive samples located in a parameter subspace defined by $\Delta_+^{ROI} = [\Delta_x^{ROI}, \Delta_y^{ROI}, X, \Delta_{\sigma_x}^{ROI}, X]$, wherein $$\Delta_x^{ROI} \in [x-\delta_x^{ROI}, x+\delta_x^{ROI}],$$

$$\Delta_y^{ROI} \in [y-\delta_y^{ROI}, y+\delta_y^{ROI}],$$

$$\Delta_{\sigma_x}^{ROI} \in [\sigma_x-\delta_{\sigma_x}^{ROI}, +\delta_{\sigma_x}^{ROI}],$$

and X represents parameters $\alpha, \sigma_y$ not learned by said ROI classifier, and said ROI classifier is trained on negative samples located in a parameter subspace defined by $\Delta_-^{ROI} = \Theta - \Delta_+^{ROI}$, wherein $\Theta$ represents an entire parameter space spanned by parameter vector $\theta$, wherein the ROI classifier detects the position and scale of the feature of interest.

5. The method of claim 4, wherein said coarse classifier is trained with positive samples from a parameter subset defined by $\Delta_+^{coarse} = [\Delta_x^{coarse}, \Delta_y^{coarse}, \Delta_\alpha^{coarse}, \Delta_{\sigma_x}^{coarse}, \Delta_{\sigma_y}^{coarse}]$, where $$\Delta_x^{coarse} \in [x-\delta_x^{coarse}, x+\delta_x^{coarse}],$$

$$\Delta_y^{coarse} \in [y-\delta_y^{coarse}, y+\delta_y^{coarse}],$$

$$\Delta_\alpha^{coarse} \in [\alpha-\delta_\alpha^{coarse}, \alpha+\delta_\alpha^{coarse}],$$

$$\Delta_{\sigma_x}^{coarse} \in [\sigma_x-\delta_{\sigma_x}^{coarse}, \sigma_x+\delta_{\sigma_x}^{coarse}],$$

$$\Delta_{\sigma_y}^{coarse} \in [\sigma_y-\delta_{\sigma_y}^{coarse}, \sigma_y+\delta_{\sigma_y}^{coarse}],$$

wherein $\delta^{coarse} < \delta^{ROI}$ for all parameters, and wherein said coarse classifier is trained with negative samples in a parameter subspace defined by $\Delta_-^{coarse} = \Delta_-^{coarse} - \Delta_+^{coarse}$.

6. The method of claim 5, wherein said fine classifier is trained with positive samples from a parameter subset defined by $\Delta_+^{fine} = [\Delta_x^{fine}, \Delta_y^{fine}, \Delta_\alpha^{fine}, \Delta_{\sigma_x}^{fine}, \Delta_{\sigma_y}^{fine}]$, wherein $$\Delta_x^{fine} \in [x-\delta_x^{fine}, x+\delta_x^{fine}],$$

$$\Delta_y^{fine} \in [y-\delta_y^{fine}, y+\delta_y^{fine}],$$

$$\Delta_\alpha^{fine} \in [\alpha-\delta_\alpha^{fine}, \alpha+\delta_\alpha^{fine}],$$

$$\Delta_{\sigma_x}^{fine} \in [\sigma_x-\delta_{\sigma_x}^{fine}, \sigma_x+\delta_{\sigma_x}^{fine}],$$

$$\Delta_{\sigma_y}^{fine} \in [\sigma_y-\delta_{\sigma_y}^{fine}, \sigma_y+\delta_{\sigma_y}^{fine}],$$

wherein $\delta^{fine} < \delta^{coarse}$ for all parameters, and wherein said fine classifier is trained with negative samples in a parameter subspace defined by $\Delta_-^{fine} = \Delta_-^{coarse} - \Delta_+^{fine}$.

7. The method of claim 3, wherein detecting said anatomic feature of interest comprises uniformly sampling a parameter space of parameter vector $\theta$ using said ROI classifier with a sampling interval vector used for training said ROI classifier, having said coarse classifier classify positive samples identified by said ROI classifier using a smaller sampling interval vector used for training said coarse classifier, and having said fine classifier classify positive samples identified by said coarse classifier using a smaller sampling interval vector used for training said fine classifier, wherein each classifier forms a union of its positive samples with those positive samples of the previous classifier.

8. The method of claim 7, further comprising selecting a positive sample from said fine classifier with a highest probability as representing said anatomic feature of interest if said positive sample probability is greater than a predetermined threshold.

9. The method of claim 1, wherein said anatomic feature of interest is one or more of a bi-parietal diameter, a head circumference, an abdominal circumference, a femur length, a humerus length, and a crown rump length.

10. A method for detecting fetal anatomic features in ultrasound images, said method comprising the steps of:
    providing an ultrasound image of a fetus, said image comprising a plurality of intensities associated with a 2-dimensional grid;
    specifying an anatomic feature of interest to be detected in a region of interest S in said image determined by parameter vector $\theta$;

providing a sequence of probabilistic boosting tree classifiers, each with a pre-specified height and number of nodes, wherein each classifier computes a posterior probability P(y|S) where y∈{−1,+1}, with P(y=+1|S) representing a probability that region of interest S contains the feature of interest, and P(y=−1|S) representing a probability that region of interest S contains background information; and detecting said anatomic feature of interest by uniformly sampling a parameter space of parameter vector θ using a first classifier with a sampling interval vector used for training said first classifier, and having each subsequent classifier of said sequence of classifiers classify positive samples identified by a preceding classifier using a smaller sampling interval vector used for training said preceding classifier, wherein each classifier forms a union of its positive samples with those positive samples of the preceding classifier.

11. The method of claim 10, further comprising training said sequence of probabilistic boosting tree classifiers on a plurality of training ultrasound images using a set of positive feature samples and a set of negative feature samples generated for each of said plurality of images by randomly sampling a parameter subspace, wherein a sampling interval for each classifier is finer than a sampling interval for a preceding classifier, and a sampling region for each classifier contains the sampling region for each subsequent classifier.

12. The method of claim 10, wherein said region of interest (ROI) is determined by parameter vector $\theta=\lfloor x, y, \alpha, \sigma_x, \sigma_y \rfloor$ wherein (x, y) represent a top left position in said ROI, α denotes an orientation of said ROI, and $(\sigma_x, \sigma_y)$ represent a scale of said ROI.

13. The method of claim 10, further comprising selecting a positive sample from said fine classifier with a highest probability as representing said anatomic feature of interest if said positive sample probability is greater than a predetermined threshold.

14. A program storage device readable by a computer, tangibly embodying a program of instructions executable by the computer to perform the method steps for detecting fetal anatomic features in ultrasound images, said method comprising the steps of:
providing a plurality of ultrasound images of a fetus, each said image comprising a plurality of intensities associated with a 2-dimensional grid;
providing a parameter vector specifying a region of interest S containing an anatomic feature of interest for each of said plurality of images;
training a sequence of probabilistic boosting tree classifiers, each with a pre-specified height and number of nodes, wherein each classifier is trained with a set of positive feature samples and a set of negative feature samples generated for each of said plurality of images by randomly sampling a parameter subspace, wherein each classifier computes a posterior probability P(y|S) where y∈{−1,+1}, with P(y=+1|S) representing a probability that the image region S contains the feature of interest, and P(y=−1|S) representing a probability that image region S contains background information; and
detecting said anatomic feature of interest in a new ultrasound image using said probabilistic boosting tree classifiers.

15. The computer program storage device of claim 14, wherein each region of interest (ROI) S is determined by parameter vector $\theta=\lfloor x, y, \alpha, \sigma_x, \sigma_y \rfloor$, wherein (x, y) represent a top left position in said ROI, α denotes an orientation of said ROI, and $(\sigma_x, \sigma_y)$ represent a scale of said ROI.

16. The computer readable program storage device of claim 15, wherein said sequence of probabilistic boosting tree classifiers comprises an ROI classifier, a coarse classifier, and a fine classifier.

17. The computer readable program storage device of claim 16, wherein said ROI classifier is trained on positive samples located in a parameter subspace defined by $\Delta_+^{ROI}=[\Delta_x^{ROI}, \Delta_y^{ROI}, X, \Delta_{\sigma_x}^{ROI}, X]$, wherein $\Delta_x^{ROI} \in [x-\delta_x^{ROI}, x+\delta_x^{ROI}]$, $\Delta_y^{ROI} \in [y-\delta_y^{ROI}, y+\delta_y^{ROI}]$, $\Delta_{\sigma_x}^{ROI} \in [\sigma_x-\delta_{\sigma_x}^{ROI}, \sigma_x+\delta_{\sigma_x}^{ROI}]$, and X represents parameters α, $\sigma_y$ not learned by said ROI classifier, and said ROI classifier is trained on negative samples located in a parameter subspace defined by $\Delta_-^{ROI}=\Theta-\Delta_+^{ROI}$, wherein Θ represents an entire parameter space spanned by parameter vector θ, wherein the ROI classifier detects the position and scale of the feature of interest.

18. The computer readable program storage device of claim 17, wherein said coarse classifier is trained with positive samples from a parameter subset defined by $\Delta_+^{coarse}=\lfloor \Delta_x^{coarse}, \Delta_y^{coarse}, \Delta_\alpha^{coarse}, \Delta_{\sigma_x}^{coarse}, \Delta_{\sigma_y}^{coarse} \rfloor$, where $\Delta_x^{coarse} \in [x-\delta_x^{coarse}, x+\delta_x^{coarse}]$, $\Delta_y^{coarse} \in [y-\delta_y^{coarse}, y+\delta_y^{coarse}]$, $\Delta_\alpha^{coarse} \in [\alpha-\delta_\alpha^{coarse}, \alpha+\delta_\alpha^{coarse}]$, $\Delta_{\sigma_x}^{coarse} \in [\sigma_x-\delta_{\sigma_x}^{coarse}, \sigma_x+\delta_{\sigma_x}^{coarse}]$, $\Delta_{\sigma_y}^{coarse} \in [\sigma_y-\delta_{\sigma_y}^{coarse}, \sigma_y+\delta_{\sigma_y}^{coarse}]$, wherein $\delta^{coarse}<\delta^{ROI}$ for all parameters, and wherein said coarse classifier is trained with negative samples in a parameter subspace defined by $\delta_-^{coarse}=\Delta_-^{ROI}-\Delta_+^{coarse}$.

19. The computer readable program storage device of claim 18, wherein said fine classifier is trained with positive samples from a parameter subset defined by $\Delta_+^{fine}\lfloor \Delta_x^{fine}, \Delta_y^{fine}, \Delta_\alpha^{fine}, \Delta_{\sigma_x}^{fine}, \Delta_{\sigma_y}^{fine} \rfloor$, wherein $\Delta_x^{fine} \in [x-\delta_x^{fine}, x+\delta_x^{fine}]$, $\Delta_y^{fine} \in [y-\delta_y^{fine}, y+\delta_y^{fine}]$, $\Delta_\alpha^{fine} \in [\alpha-\delta_\alpha^{fine}, \alpha+\delta_\alpha^{fine}]$, $\Delta_{\sigma_x}^{fine} \in [\sigma_x-\delta_{\sigma_x}^{fine}, \sigma_x+\delta_{\sigma_x}^{fine}]$, $\Delta_{\sigma_y}^{fine} \in [\sigma_y-\delta_{\sigma_y}^{fine}, \sigma_y+\delta_{\sigma_y}^{fine}]$, wherein $\delta^{fine}<\delta^{coarse}$ for all parameters, and wherein said fine classifier is trained with negative samples in a parameter subspace defined by $\Delta_-^{fine}=\Delta_-^{coarse}-\Delta_+^{fine}$.

20. The computer readable program storage device of claim 16, wherein detecting said anatomic feature of interest comprises uniformly sampling a parameter space of parameter vector θ using said ROI classifier with a sampling interval vector used for training said ROI classifier, having said coarse classifier classify positive samples identified by said ROI classifier using a smaller sampling interval vector used for training said coarse classifier, and having said fine classifier classify positive samples identified by said coarse classifier using a smaller sampling interval vector used for training said fine classifier, wherein each classifier forms a union of its positive samples with those positive samples of the previous classifier.

21. The computer readable program storage device of claim 20, the method further comprising selecting a positive sample from said fine classifier with a highest probability as representing said anatomic feature of interest if said positive sample probability is greater than a predetermined threshold.

22. The computer readable program storage device of claim 14, wherein said anatomic feature of interest is one or more of a bi-parietal diameter, a head circumference, an abdominal circumference, a femur length, a humerus length, and a crown rump length.

23. A program storage device readable by a computer, tangibly embodying a program of instructions executable by the computer to perform the method steps for detecting fetal anatomic features in ultrasound images, said method comprising the steps of:
   providing an ultrasound image of a fetus, said image comprising a plurality of intensities associated with a 2-dimensional grid;
   specifying an anatomic feature of interest to be detected in a region of interest S in said image determined by parameter vector $\theta$;
   providing a sequence of probabilistic boosting tree classifiers, each with a pre-specified height and number of nodes, wherein each classifier computes a posterior probability $P(y|S)$ where $y \in \{-1,+1\}$, with $P(y=+1|S)$ representing a probability that region of interest S contains the feature of interest, and $P(y=-1|S)$ representing a probability that region of interest S contains background information; and
   detecting said anatomic feature of interest by uniformly sampling a parameter space of parameter vector $\theta$ using a first classifier with a sampling interval vector used for training said first classifier, and having each subsequent classifier of said sequence of classifiers classify positive samples identified by a preceding classifier using a smaller sampling interval vector used for training said preceding classifier, wherein each classifier forms a union of its positive samples with those positive samples of the preceding classifier.

24. The computer readable program storage device of claim 23, the method further comprising training said sequence of probabilistic boosting tree classifiers on a plurality of training ultrasound images using a set of positive feature samples and a set of negative feature samples generated for each of said plurality of images by randomly sampling a parameter subspace, wherein a sampling interval for each classifier is finer than a sampling interval for a preceding classifier, and a sampling region for each classifier contains the sampling region for each subsequent classifier.

25. The computer readable program storage device of claim 23, wherein said region of interest (ROI) is determined by parameter vector $\theta = [x, y, \alpha, \sigma_x, \sigma_y]$, wherein (x, y) represent a top left position in said ROI, $\alpha$ denotes an orientation of said ROI, and $(\sigma_x, \sigma_y)$ represent a scale of said ROI.

26. The computer readable program storage device of claim 23, the method further comprising selecting a positive sample from said fine classifier with a highest probability as representing said anatomic feature of interest if said positive sample probability is greater than a predetermined threshold.

* * * * *